United States Patent [19]

Katner

[11] 4,346,076
[45] Aug. 24, 1982

[54] BIS-TETRAZOYLMETHYL SUBSTITUTED CEPHALOSPORIN ANTIBIOTICS

[75] Inventor: Allen S. Katner, Indianapolis, Ind.

[73] Assignee: Eli Lilly and Company, Indianapolis, Ind.

[21] Appl. No.: 187,859

[22] Filed: Sep. 17, 1980

[51] Int. Cl.³ ............... A61K 31/545; C07D 501/56
[52] U.S. Cl. .................................. 424/246; 544/26; 544/27; 544/21
[58] Field of Search .................. 544/27, 26, 21; 424/246

[56] References Cited

U.S. PATENT DOCUMENTS

| | | | |
|---|---|---|---|
| 4,080,498 | 3/1978 | Numata et al. | 544/27 |
| 4,100,346 | 7/1978 | Gottstein et al. | 544/27 |
| 4,109,085 | 8/1978 | Barth | 544/30 |
| 4,113,942 | 9/1978 | Barth | 544/23 |
| 4,121,040 | 10/1978 | Barth | 544/28 |
| 4,129,732 | 12/1978 | Barth | 544/23 |
| 4,286,089 | 8/1981 | Berges | 544/27 |
| 4,288,436 | 9/1981 | Takaya et al. | 544/27 |

OTHER PUBLICATIONS

H. Faubl. Tetrahedron Letters No. 6, pp. 491–494, Permagon Press Ltd., 1979.

Primary Examiner—Paul M. Coughlan, Jr.
Attorney, Agent, or Firm—William B. Scanlon; Arthur R. Whale

[57] ABSTRACT

7β-Acylamino-3-cephem-4-carboxylic acids substituted in the 3-position with a bis-tetrazolemethylthiomethyl group and the corresponding 7α-methoxy cephalosporins represented by the formula t,0010

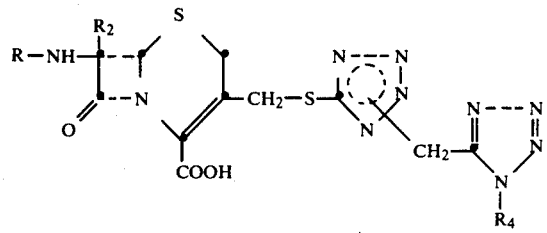

wherein R is an acyl group, $R_2$ is H or $OCH_3$ and $R_4$ is H or $C_1$–$C_3$ alkyl; are broad spectrum antibiotics useful in the treatment and control of microorganisms pathogenic to man and animals. 7β-Amino nucleus compounds represented when R is hydrogen are intermediates useful in the preparation of the antibiotics where R is acyl.

32 Claims, No Drawings

BIS-TETRAZOYLMETHYL SUBSTITUTED CEPHALOSPORIN ANTIBIOTICS

SUMMARY

7β-Acylamino cephalosporin compounds substituted in the 3-position with a 1-(1H-tetrazol-5-yl-methyl)-1H-tetrazol-5-ylthiomethyl group of the formula

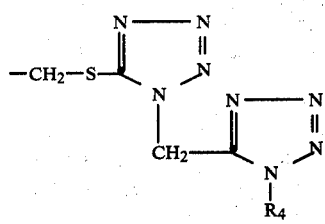

or a 2-(1H-tetrazol-5-yl-methyl)-2H-tetrazol-5-yl-thiomethyl group of the formula

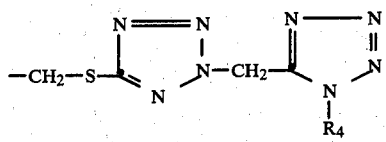

wherein in each of the above formulas $R_4$ is hydrogen, or $C_1$-$C_3$ alkyl, are broad spectrum antibiotics which inhibit the growth of microorganisms pathogenic to man and animals. The compounds are useful when administered parenterally in suitable pharmaceutical dosage forms. Compounds of the invention wherein the 3 substituent is the 1-(1H-tetrazol-5-yl-methyl)-1H-tetrazol-5-yl-thiomethyl group provide effective blood levels of extended duration in animals.

The bis-tetrazolylmethyl substituted cephalosporins of this invention are prepared by several preparative methods. For example, 7-aminocephalosporanic acid (7-ACA) is reacted with the appropriate bis-tetrazolmethyl thiol to form the 7-amino-3-bis-tetrazolmethyl thiomethyl-3-cephem-4-carboxylic acid, and the latter intermediate is acylated at the 7-position amino group to provide a 7-acylamino substituted cephalosporin. Alternatively, a 7-acylaminocephalosporanic acid can be reacted with the appropriate bis-tetrazolmethyl thiol to provide a compound of the invention. Lastly, a 7-acylaminocephalosporanic acid is reacted with 1-cyanomethyl-1H-tetrazol-5-yl-thiol to provide the corresponding 7-acylamino-3-(1-cyanomethyl-1H-tetrazol-5-yl-thiomethyl)-3-cephem-4-carboxylic acid intermediate, and the latter is reacted at the cyano group of the 3-tetrazole moiety with an appropriate azide to form the bis-tetrazolmethyl compound of the invention.

The invention also provides the bis-tetrazolmethyl thiomethyl substituted cephalosporin nucleus having an unacylated amino group in the 7-position. This 7-amino nucleus compound is useful in preparing the 7-acylaminocephalosporins of the invention as described above.

BACKGROUND OF THE INVENTION

Cephalosporin antibiotics having various heterocyclic thiomethyl substituents in the 3-position are known. For example, Takano et al., U.S. Pat. No. 3,516,997, describe tetrazolthiol and thiadiazolthiol substituted cephalosporins having a heterocyclic acylamino group in the 7-position; Ryan, U.S. Pat. No. 3,641,021 describes tetrazolthiol and thiadiazolthiol substituted cephalosporins having a mandeloyl or phenylglycyl substituent in the 7-position; Breuer, et al., U.S. Pat. No. 4,110,535, describe certain cephalosporin compounds having a 3-oxopyridazinylthiomethyl substituent in the 3-position; Berges, U.S. Pat. No. 4,107,173, describes cephalosporin compounds having as the 3' substituent a 3-sulfomethyl-1,2,4-triazol-5-ylthiomethyl substituent; Toshiyasu, et al., U.S. Pat. No. 4,103,008, describe cephalosporin compounds substituted in the 7-position by a dioxopiperazine-1-yl-carbonylamino substituent and in the 3-position by a substituted or unsubstituted 1,3,4-thiadiazol-2-ylthiomethyl substituent; Berges, U.S. Pat. No. 4,101,656, describes 7-acylamino substituted cephalosporins having a tetrazolthiomethyl substituent in the 3-position which is substituted with an alkylsulfonamidoalkyl group; Gottstein, et al., U.S. Pat. No. 4,100,346, describe certain o-aminophenylacetamido substituted cephalosporins having a tetrazolthiomethyl substituent in the 3-position which is substituted with a carboxyethyl or carboxypropyl substituent; Numata, et al., U.S. Pat. No. 4,080,498, disclose a 2-aminothiazolacetamido cephalosporin substituted in the 3-position with a heterocyclic thiomethyl group; Dunn, et al., U.S. Pat. No. 3,968,226, describe numerous 3-heterocyclicthiomethyl substituted cephalosporins; Naito, et al., U.S. Pat. No. 4,082,912, disclose 7-acylamidocephalosporins having the fused heterocyclic, (2-carboxyalkyl)-2,3-dihydro-S-triazolo[4,3-b]pyridazin-3-one-6-ylmethyl group in the 3-position; British patent specification No. 1,525,626 describes certain cephalosporin compounds having a 1-carboxymethyl-1H-tetrazol-5-thiomethyl substituent in the 3-position; Dunn, et al., U.S. Pat. No. 3,985,739, describe 7-phenylglycyl or 7-mandeloyl substituted cephalosporins having in the 3-position a 1,3,4- or a 1,2,3-triazolthiomethyl substituent; Naito, et al., U.S. Pat. No. 3,985,738, describe 7-mandelamidocephalosporins having in the 3-position a tetrazolo[4,5-b]pyridazin-6-ylthiomethyl substituent; and Barth, U.S. Pat. No. 3,966,719, discloses cephalosporin compounds wherein the 4-carboxy group is replaced with a tetrazol-5-yl group.

3-Heterocyclicthiol substituted methyl cephalosporins are generally prepared by the displacement of the acetoxy group of a 3-acetoxymethyl-3-cephem, or the halogen of a 3-halomethyl-3-cephem compound, with the desired heterocyclic thiol. Hatfield, U.S. Pat. No. 4,144,391, describes a non-aqueous displacement method for the preparation of 3-heterocyclicthiomethyl substituted cephalosporins.

This invention is concerned with broad spectrum cephalosporin antibiotics which differ structurally from the known cephalosporins. In particular, this invention relates to 7-amino and 7-acylamino cephalosporin compounds substituted in the 3-position of the dihydrothiazine ring with a bis-tetrazolylmethyl group. In particular, the bis-tetrazolylmethyl substituents are the 1-(1H-tetrazol-5-ylmethyl)-1H-tetrazol-5-ylthio group and the isomeric 2-(1H-tetrazol-5-ylmethyl)-2H-tetrazol-5-ylthio group.

DETAILED DESCRIPTION

The cephalosporin compounds of this invention are represented by the following general formula.

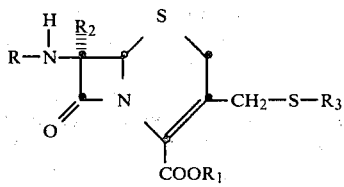

wherein $R_3$ is

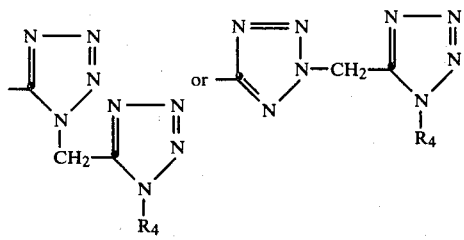

and $R_4$ is hydrogen, or $C_1$–$C_3$ alkyl;

wherein

R is hydrogen or an acyl group derived from a carboxylic acid;

$R_1$ is hydrogen or a carboxy-protecting group which is readily removed by hydrolytic or hydrogenolysis methods;

and $R_2$ is hydrogen or methoxy.

The term "acyl group derived from a carboxylic acid" refers to the 6- and 7-acyl portions of the side chain acylamino substituents of the known penicillin and cephalosporin antibiotics. Examples of carboxylic acids providing such acyl groups are the alkylcarboxylic acids such as formic acid, acetic acid, propionic acid, n-butyric acid, iso-butyric acid, n-valeric acid, trimethylacetic acid, caproic acid, n-heptylic acid, caprylic acid, and the like; the alkenoic acids, for example, acrylic acid, crotonic acid, and the like; the substituted alkyl carboxylic acids wherein the substituent is hydroxy, halogen, or cyano, for example, chloroacetic acid, bromoacetic acid, bromobutyric acid, chloropropionic acid, hydroxyacetic acid, gamma-hydroxybutyric acid, cyanoacetic acid, cyanopropionic acid, and cyanobutyric acid; the aromatic carboxylic acids, such as benzoic acid and substituted benzoic acids, for example, the toluic acids, p-chlorobenzoic acid, 3,4-dichlorobenzoic acid, 3-fluorobenzoic acid, p-hydroxybenzoic acid, the carboxy-substituted benzoic acids, for example, phthalic acid and terephthalic acid, p-aminobenzoic acid, m-aminobenzoic acid, and the acetylated derivatives thereof, 3,4-dihydroxybenzoic acid, 3-chloro-4-hydroxybenzoic acid, o-methoxybenzoic acid, p-methoxybenzoic acid, p-ethoxybenzoic acid, and like substituted benzoic acids; the aryl alkanoic acids such as phenylacetic acid and the substituted phenylacetic acids for example, 4-hydroxyphenylacetic acid, 4-chlorophenylacetic acid, 2-aminomethylphenylacetic acid, 3-carboxymethylphenylacetic acid and the like; the aryl alkanoic acids wherein the aryl portion is separated from the alkyl portion by a hetero atom such as phenoxyacetic acid, and the substituted phenoxyacetic acids, for example, p-chlorophenoxyacetic acid, p-hydroxyphenoxyacetic acid, phenylmercaptoacetic acid, and the halogenated derivatives thereof, for example, 3,4-dichlorophenylmercaptoacetic acid, p-chlorophenylmercaptoacetic acid, p-fluorophenylmercaptoacetic acid, 3,4-dimethylphenylmercaptoacetic acid, and the like; the aryl acetic acids, wherein the alkyl portion is substituted, for example, phenylglycine, mandelic acid, phenylmalonic acid, α-sulfophenylacetic acid, and such acids wherein the aromatic ring bears a substituent, for example, halogen, hydroxy, carboxy, alkyl, for example, methyl trifluoromethyl, alkoxy, for example, methoxy and ethoxy, amino and substituted amino, such as acetamido, and like substituted acids; the heteroaryl acetic acids, wherein the heteroatom contains one or more oxygen, nitrogen, or sulfur atoms along with carbon in the hetero ring, for example, the 5- and 6-membered heterocyclic aryl acetic acids, such as thiopheneacetic acid, furaneacetic acid, pyridylacetic acid, and the hydroxy-substituted pyridylacetic acids, for example, 4-hydroxypyridyl-3-acetic acid, imidazolacetic acid, thiazoleacetic acid, oxazoleacetic acid, 1,3,4-thiadiazolacetic acid, 1,3,4-oxadiazolacetic acid, isooxazoleacetic acid, and the like; and the benzheterocyclic acetic acids, for example, 2-benzothienyl acetic acid, 2-benzofuran acetic acid, and like heterocyclic aryl acetic acids. Acyl moieties represented by the term "R" in the above structural formula can also be aromatic glyoxylic acid derivatives, for example, the oximes of phenylglyoxylic acid, furanglyoxylic acid, 1,3-thiazoleglyoxylic acid, 1,3-oxazoleglyoxylic acid, and the substituted derivatives thereof, for example, 2-amino-1,3-thiazoleglyoxylic acid oxime, and the derivatives of the oximino function thereof, for example, the lower alkyl oxime derivatives such as the methoxyimino and ethoxyimino derivatives. Also, R in the above formula represents the acyl portion of phenylglycines wherein the amino group is substituted, for example, by a carbamoyl group or a substituted carbamoyl group, wherein the nitrogen of the carbamoyl group is substituted with an acyl moiety, for example, acetyl, benzoyl, cinnamoyl, furoyl, thenoyl, and the like. Also, the amino group of the phenylglycine can be substituted with a cyclic urea function, for example, the amino group can be substituted with a 1-imidazolidone-2-carbonyl group or with a 1-(4-ethylpiperazine-2,3-dione)carbonyl group.

In the above formula, $R_1$ is hydrogen or a carboxy-protecting group which is readily removed under hydrolysis conditions or by hydrogenolysis. Such groups are well known in the cephalosporin art and include the readily cleaved ester groups for example, benzyl, diphenylmethyl, p-nitrobenzyl, p-methoxybenzyl, phenacyl, halogenated phenacyl, haloalkyl, for example, iodomethyl, 2,2,2-trichloroethyl, and 2,2,2-tribromoethyl; branched alkyl, alkenyl, and alkynyl esters, for example, t-butyl, 3-methylbutene-1-3-yl, and isopentenyl.

When in the above formula, $R_1$ is hydrogen, the compounds of the invention can be converted to pharmaceutically acceptable salts, for example, the alkali metal and alkaline earth metal salts such as the sodium salt, the potassium salt, the lithium salt, and the calcium salt; amine salts such as those formed with pharmaceutically acceptable amines such as procaine, abietyl amine, the ethanolamines, such as monoethanolamine and diethanolamine, and like amine and metal salts, and the ammonium salt. The salts can be formulated into pharmaceutically useful parenteral dosage forms for administration of the antibiotics.

Preferred compounds of the invention are those represented by the above general formula wherein $R_3$ is a 1-(1H-tetrazol-5-ylmethyl)-1H-tetrazol-5-yl group wherein the NH group of the terminal tetrazole can be substituted with $C_1$-$C_3$ alkyl;

A further preferred group of compounds of the invention are represented by the following structural formula 1.

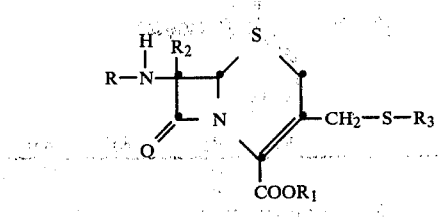

wherein R is hydrogen or an acyl group of the formula

wherein $R^1$ is $C_1$-$C_4$ alkyl, $C_1$-$C_4$ alkyl substituted by halogen or cyano; or R is an aroyl or aralkanoyl group of the formula

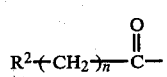

wherein $R^2$ is phenyl or a mono substituted phenyl group of the formula

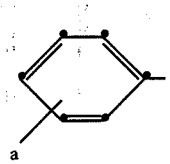

wherein a is halogen, amino, hydroxy, $C_1$-$C_4$ alkyl, $C_1$-$C_4$ alkoxy, cyano, hydroxymethyl, aminomethyl, carboxamido, carboxymethyl, or $C_1$-$C_4$ alkoxycarbonylmethyl;

or $R^2$ is a di- or tri-substituted phenyl group of the formula

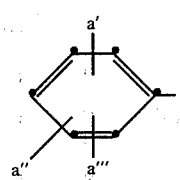

wherein a', a", and a''' are independently hydrogen, halogen, hydroxy, $C_1$-$C_4$ alkyl, or $C_1$-$C_4$ alkoxy; and n is 0 or 1;

or R is a heteroarylalkanoyl group of the formula

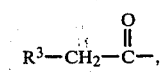

wherein $R^3$ is

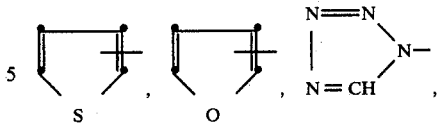

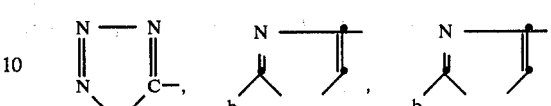

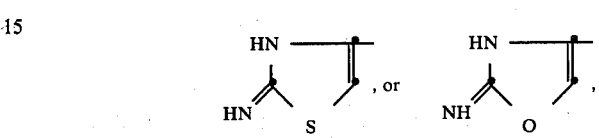

wherein each b is amino, protected amino, $C_1$-$C_3$ alkyl or phenyl;

or R is an aryloxyacetyl or arylthioacetyl group of the formula

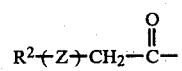

wherein $R^2$ has the same meanings as defined above and Z is O or S;

or R is an aralkanoyl or heteroarylalkanoyl substituted group of the formula

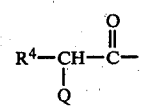

wherein $R^4$ is $R^2$, as defined above, and in addition is thienyl, furyl, or 1,4-cyclohexadienyl; Q is hydroxy, formyloxy, carboxy, the sulfo group —$SO_3H$, or amino;

or R is an oximino-substituted aralkanoyl or heteroarylalkanoyl group of the formula

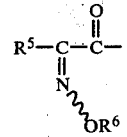

wherein $R^5$ is $R^2$ and $R^3$ as each is defined above, and $R^6$ is hydrogen or $C_1$-$C_3$ alkyl;

or R is a group of the formula

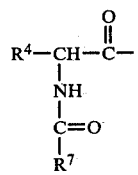

wherein $R^7$ is hydroxyphenyl or hydroxypyridyl or a group of the formula

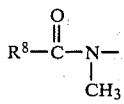

wherein R⁸ is C₁–C₄ alkylamino, phenyl, furyl, styryl, nitrostyryl, or chlorostyryl; or R⁷ is a group of the formula

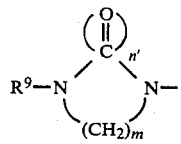

wherein n' is 1 or 2 and m is 2 or 3 with the limitation that when n' is 2, m is 2; and R⁹ is hydrogen, C₁–C₃ alkyl, or C₁–C₃ alkylsulfonyl;
R₁ is hydrogen or a carboxy protecting group;
R₂ is hydrogen or methoxy;
R₃ is a bis-tetrazolyl methyl group of the formula

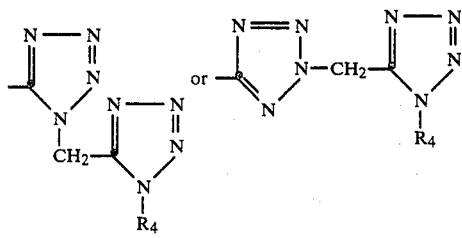

wherein R₄ is hydrogen, or C₁–C₃ alkyl; and when R₁ is hydrogen the pharmaceutically acceptable non-toxic salts thereof.

Examples of the foregoing preferred compounds are described below in Table 1.

TABLE 1
Bis-Tetrazolemethyl Cephalosporins

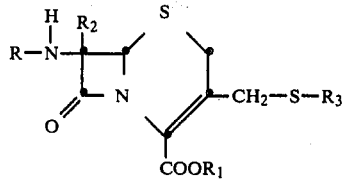

| R | R₁ | R₂ | R₃¹ | (R₄) |
|---|---|---|---|---|
| R = R¹—C(O)— | | | | |
| acetyl | H | H | A | H |
| " | Na | OCH₃ | A | CH₃ |
| " | H | H | B | CH₃ |
| propionyl | H | H | A | H |
| butyryl | H | H | A | H |
| chloroacetyl | H | H | A | H |
| " | H | OCH₃ | A | CH₃ |
| " | H | H | B | H |
| cyanoacetyl | H | H | A | H |
| " | H | OCH₃ | A | H |
| " | H | H | B | CH₃ |

TABLE 1-continued
Bis-Tetrazolemethyl Cephalosporins

| R | R₁ | R₂ | R₃¹ | (R₄) |
|---|---|---|---|---|
| R = R²—(CH₂)ₙ—C(O)— (n = 0) | | | | |
| benzoyl | H | H | A | H |
| " | H | H | B | H |
| " | H | H | A | CH₃ |
| p-chlorobenzoyl | H | H | A | CH₃ |
| 2,6-dimethoxybenzoyl | H | H | A | H |
| p-hydroxybenzoyl | H | H | A | H |
| p-toluyl | H | H | A | H |
| p-anisoyl | H | H | B | H |
| m-cyanobenzoyl | H | H | B | CH₃ |
| p-methoxycarbonylbenzoyl | H | H | A | H |
| R = R²—(CH₂)ₙ—C(O)— (n = 1) | | | | |
| phenylacetyl | H | H | A | H |
| " | H | OCH₃ | A | CH₃ |
| " | H | H | B | H |
| p-chlorophenylacetyl | H | H | A | H |
| p-methylphenylacetyl | H | H | B | H |
| 3,4-dimethylphenylacetyl | H | H | A | H |
| o-aminomethylphenylacetyl | H | H | A | CH₃ |
| o-aminomethylphenylacetyl | H | H | B | H |
| p-hydroxymethylphenylacetyl | H | H | A | H |
| p-hydroxymethylphenylacetyl | H | H | A | H |
| p-carboxamidophenylacetyl | H | H | A | H |
| p-methoxyphenylacetyl | Na | H | A | H |
| p-methoxyphenylacetyl | H | OCH₃ | B | CH₃ |
| 3,4-dimethoxyphenylacetyl | H | H | A | H |
| p-cyanophenylacetyl | H | H | A | CH₃ |
| p-ethoxyphenylacetyl | H | H | B | H |
| p-isopropoxyphenylacetyl | H | H | A | CH₃ |
| 3-ethylphenylacetyl | H | H | A | CH₃ |
| 2,6-dimethylphenylacetyl | H | H | A | CH₃ |
| 2,6-dimethoxyphenylacetyl | H | OCH₃ | A | CH₃ |
| p-bromophenylacetyl | H | H | B | H |
| m-fluorophenylacetyl | H | H | A | H |
| 3,4-dihydroxyphenylacetyl | H | H | A | CH₃ |
| 3-chloro-4-hydroxyphenylacetyl | H | H | A | H |
| 3,5-dichloro-4- | H | H | B | H |

TABLE 1-continued
Bis-Tetrazolemethyl Cephalosporins

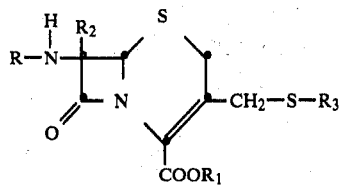

| R | $R_1$ | $R_2$ | $R_3{}^1$ | ($R_4$) |
|---|---|---|---|---|
| hydroxyphenylacetyl 3-methoxy-4-hydroxyphenylacetyl | H | H | A | CH₃ |
| 3-methyl-4-hydroxyphenylacetyl | H | H | B | H |
| o-ethoxyphenylacetyl | H | OCH₃ | A | H |
| p-fluorophenylacetyl | H | H | A | H |
| p-carboxyphenylacetyl | H | H | H | CH₃ |
| 3-bromo-4-methoxyphenylacetyl | H | H | B | H |
| p-t-butylphenylacetyl | H | H | A | CH₃ |

$$R = R^3-CH_2-\overset{O}{\underset{\|}{C}}-$$

| R | $R_1$ | $R_2$ | $R_3{}^1$ | ($R_4$) |
|---|---|---|---|---|
| 2-thienylacetyl | H | H | A | H |
| " | H | OCH₃ | A | H |
| " | pNB | H | B | H |
| 3-thienylacetyl | H | H | A | H |
| 2-furylacetyl | H | H | A | CH₃ |
| " | H | OCH₃ | B | H |
| 1H-tetrazol-1-ylacetyl | H | H | A | CH₃ |
| 1H-tetrazol-1-ylacetyl | H | OCH₃ | A | CH₃ |
| 1H-tetrazol-1-ylacetyl | H | H | B | H |
| 2H-tetrazol-5-ylacetyl | H | H | A | H |
| 2H-tetrazol-5-ylacetyl | H | OCH₃ | A | H |
| 2H-tetrazol-5-ylacetyl | H | OCH₃ | B | CH₃ |
| 1,3-thiazol-4-acetyl | H | H | A | H |
| 1,3-oxazol-4-ylacetyl | H | H | A | CH₃ |
| 2-methyl-1,3-thiazol-4-ylacetyl | H | H | B | H |
| 2-phenyl-1,3-thiazol-4-ylacetyl | H | OCH₃ | A | CH₃ |
| 2-phenyl-1,3-oxazol-4-ylacetyl | H | OCH₃ | B | CH₃ |
| 2-amino-1,3-thiazol-4-ylacetyl | H | H | A | H |
| 2-amino-1,3-thiazol-4-ylacetyl | Na | H | A | CH₃ |
| 2-amino-1,3-thiazol-4-ylacetyl | H | OCH₃ | A | H |
| 2-amino-1,3-thiazol-4-ylacetyl | H | H | B | H |

$$R = R^2-(Z)-CH_2-\overset{O}{\underset{\|}{C}}-$$

| R | $R_1$ | $R_2$ | $R_3{}^1$ | ($R_4$) |
|---|---|---|---|---|
| phenoxyacetyl | H | H | A | H |
| " | H | H | A | CH₃ |
| " | H | H | B | H |
| " | H | OCH₃ | A | H |
| p-chlorophenoxyacetyl | H | H | A | H |
| 3,4-dichlorophenoxyacetyl | H | H | B | H |

TABLE 1-continued
Bis-Tetrazolemethyl Cephalosporins

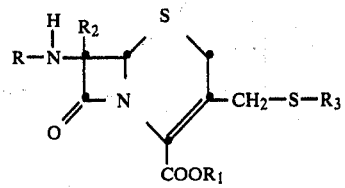

| R | $R_1$ | $R_2$ | $R_3{}^1$ | ($R_4$) |
|---|---|---|---|---|
| p-methylphenoxyacetyl | H | OCH₃ | A | CH₃ |
| p-fluorophenoxyacetyl | H | H | A | H |
| p-methoxyphenoxyacetyl | H | H | B | H |
| p-hydroxyphenoxyacetyl | H | OCH₃ | A | H |
| 3-chloro-4-methoxyphenoxyacetyl | H | H | B | H |
| 3,5-dichloro-4-hydroxyphenoxyacetyl | H | H | A | CH₃ |
| phenylthioacetyl | H | H | A | H |
| " | H | H | B | H |
| " | H | OCH₃ | A | H |
| p-chlorophenylthioacetyl | H | H | A | H |
| 3,4-dichlorophenylthioacetyl | H | H | B | H |
| 3,5-dichlorophenylthioacetyl | H | H | A | CH₃ |
| p-fluorophenylthioacetyl | H | H | A | H |
| p-methylphenylthioacetyl | H | H | B | H |
| 3-hydroxy-4-methylphenylthioacetyl | H | H | A | H |
| p-ethoxyphenylthioacetyl | H | OCH₃ | A | H |

$$R = R^4-\underset{Q}{\overset{\displaystyle}{C}}H-\overset{O}{\underset{\|}{C}}-$$

| R | $R_1$ | $R_2$ | $R_3{}^1$ | ($R_4$) |
|---|---|---|---|---|
| phenylglycyl | H | H | A | H |
| " | H | OCH₃ | A | H |
| p-hydroxyphenylglycyl | H | H | A | H |
| 3-chloro-4-hydroxyphenylglycyl | H | H | A | H |
| 3,5-dichloro-4-hydroxyphenylglycyl | H | H | A | H |
| mandeloyl | H | H | A | H |
| " | H | H | B | H |
| " | H | OCH₃ | A | CH₃ |
| α-carboxyphenylacetyl | H | H | A | H |
| α-carboxyphenylacetyl | H | H | B | H |
| α-carboxyphenylacetyl | H | OCH₃ | A | H |
| α-carboxy-4-hydroxyphenylacetyl | H | OCH₃ | A | H |
| α-carboxy-4-hydroxyphenylacetyl | H | OCH₃ | B | H |
| α-carboxy-4-hydroxyphenylacetyl | H | OCH₃ | B | CH₃ |
| α-sulfophenylacetyl | H | H | A | H |
| " | H | H | B | H |
| " | H | OCH₃ | A | H |
| α-amino-2-thienylacetyl | H | H | A | H |
| α-amino-2-thienylacetyl | H | H | B | H |
| α-amino-2-furylacetyl | H | H | A | CH₃ |

TABLE 1-continued
Bis-Tetrazolemethyl Cephalosporins

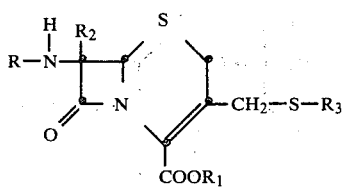

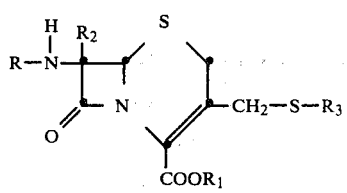

| R | $R_1$ | $R_2$ | $R_3{}^1$ | $(R_4)$ |
|---|---|---|---|---|

$$R = R^5 - \overset{\underset{\displaystyle N}{\|}}{C} - \overset{O}{\overset{\|}{C}} -$$
$$\phantom{R = R^5 - C -}\underset{OR^6}{}$$

| R | $R_1$ | $R_2$ | $R_3{}^1$ | $(R_4)$ |
|---|---|---|---|---|
| α-hydroxyimino-phenylacetyl | H | H | A | H |
| α-hydroxyimino-phenylacetyl | H | H | B | H |
| α-methoximino-phenylacetyl | H | H | A | H |
| α-hydroxyimino-2-furylacetyl | H | H | A | H |
| α-hydroxyimino-2-furylacetyl | H | OCH₃ | A | H |
| α-methoximino-2-furylacetyl | H | H | A | H |
| α-methoximino-2-thienylacetyl | H | H | A | H |
| α-hydroxyimino-(2-amino-1,3-thiazol-4-yl)acetyl | H | H | A | H |
| α-hydroxyimino-(2-amino-1,3-thiazol-4-yl)acetyl | Na | H | A | CH₃ |
| α-hydroxyimino-(2-amino-1,3-thiazol-4-yl)acetyl | H | H | B | H |
| αhydroximino-(2-amino-1,3-thiazol-4-yl)acetyl | H | OCH₃ | A | H |
| α-methoximino-(2-amino-1,3-thiazol-4-yl)acetyl | H | H | A | H |
| α-methoximino-(2-amino-1,3-thiazol-4-yl)acetyl | H | H | A | CH₃ |
| α-methoximino-(2-amino-1,3-thiazol-4-yl)acetyl | H | H | B | H |
| α-methoximino-(2-amino-1,3-thiazol-4-yl)acetyl | H | OCH₃ | A | H |

$$R = R^4 - \underset{\underset{\displaystyle R^7}{\underset{\displaystyle |}{\underset{\displaystyle C=O}{\underset{\displaystyle |}{\underset{\displaystyle NH}{|}}}}}}{CH} - \overset{O}{\overset{\|}{C}} -$$

| R | $R_1$ | $R_2$ | $R_3{}^1$ | $(R_4)$ |
|---|---|---|---|---|
| α-(4-hydroxybenz-amido)phenylacetyl | H | H | A | H |
| α-(2-hydroxybenz-amino)phenylacetyl | H | H | A | H |
| α-(2-hydroxybenz-amido)-2-thienyl-acetyl | H | H | A | CH₃ |
| α-(2,3-dihydroxy-benzamido)phenyl-acetyl | H | H | A | H |
| α-(4-hydroxybenz-amido)-4-hydroxy-phenylacetyl | H | H | A | H |
| α-(4-hydroxy-pyridine-3-car-boxamido)phenyl-acetyl | H | H | A | CH₃ |
| α-(4-hydroxy-pyridine-3-car-boxamido)phenyl-acetyl | H | H | B | H |
| α-(4-hydroxy-pyridine-3-car-boxamido)phenyl-acetyl | H | H | A | H |
| α-(3-methylcar-bamoyl-3-methyl-1-ureido)-α-phenyl-acetyl | H | H | A | H |
| α-(3-methylcar-bamoyl-3-methyl-1-ureido)-α-(4-hydroxyphenyl)-acetyl | H | H | A | H |
| α-(3-benzoyl-3-methyl-1-ureido)-α-phenylacetyl | H | H | A | CH₃ |
| α-[3-(o-chloro-benzoyl)-3-methyl-1-ureido]-α-(2-thienyl)acetyl | H | H | A | H |
| α-[3-(2-furoyl)-3-methyl-1-ureido]-α-phenylacetyl | H | H | B | H |
| α-[3-(2-thienoyl)-3-methyl-1-ureido]-α-phenylacetyl | H | H | A | H |
| α-(3-cinnamoyl-3-methyl-1-ureido)-α-phenylacetyl | H | OCH₃ | A | H |
| α-(3-cinnamoyl-3-methyl-1-ureido)-α-phenylacetyl | H | H | A | H |
| α-[3-(4-nitro-cinnamoyl)-3-methyl-1-ureido]-α-phenyl-acetyl | H | H | A | CH₃ |
| α-[3-(4-nitro-cinnamoyl)-3-methyl-1-ureido]-α-phenyl-acetyl | Na | H | B | H |
| α[3-(4-chloro-cinnamoyl)-3-methyl-1-ureido]-α-phenyl-acetyl | H | H | A | H |
| α-(imidazolidin-2-one-1-ylcarbonyl-amino)-α-phenyl-acetyl | H | H | A | H |
| α-(imidazolidin-2-one-1-ylcarbonyl-amino)-α-(4-hydroxy-phenyl)acetyl | H | H | A | CH₃ |
| α-(3-acetylimida-zolidin-2-one-1-yl-carbonylamino)-α-phenylacetyl | H | H | A | H |
| α-(3-acetylimida-zolidin-2-one-1-yl-carbonylamino)-α-phenylacetyl | H | H | B | H |

TABLE 1-continued
Bis-Tetrazolemethyl Cephalosporins

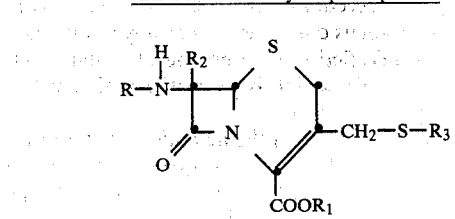

| R | R₁ | R₂ | R₃¹ | (R₄) |
|---|---|---|---|---|
| α-(3-methylsulfonylimidazolidin-2-one-1-ylcarbonylamino)-α-phenylacetyl | H | H | A | H |
| α-(3-methylsulfonylimidazolidin-2-one-1-ylcarbonylamino)-α-phenylacetyl | H | H | B | H |
| α-(3-methylsulfonylimidazolidin-2-one-1-ylcarbonylamino)-α-phenylacetyl | H | H | A | CH₃ |
| α-(4-ethylpiperazin-2,3-dione-1-ylcarbonylamino)-α-phenylacetyl | H | H | A | H |
| α-(4-ethylpiperazin-2,3-dione-1-ylcarbonylamino)-α-phenylacetyl | H | H | B | H |
| α-(4-ethylpiperazin-2,3-dione-1-ylcarbonylamino)-α-phenylacetyl | H | H | B | CH₃ |
| α-(4-ethylpiperazin-2,3-dione-1-ylcarbonylamino)-α-(4-hydroxyphenyl)-acetyl | H | H | A | H |
| α-(4-ethylpiperazin-2,3-dione-1-ylcarbonylamino)-α-(4-hydroxyphenyl)-acetyl | H | H | A | CH₃ |
| α-(4-methylpiperazin-2,3-dione-1-ylcarbonylamino)-α-(2-thienyl)acetyl | H | H | A | H |
| α-(piperazin-2,3-dione-1-ylcarbonylamino)-α-phenylacetyl | H | H | A | H |

¹A = 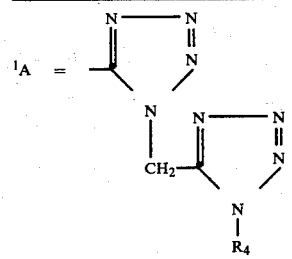

B = 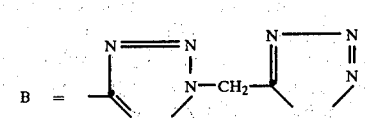

The compounds of this invention have the normal stereochemistry of the cephalosporin antibiotics with the 7-position side chain, R, having the β-configuration while the term "R₂", the 7-methoxy group, has the α-configuration.

The compounds of the invention, represented by the above formula wherein R is an acyl group, are prepared by the N-acylation of a 7-amino-3-(bis-tetrazolmethyl) compound of the formula 1 wherein R is H. The 7-amino nucleus compounds are represented by the following structural formulas 2 and 3.

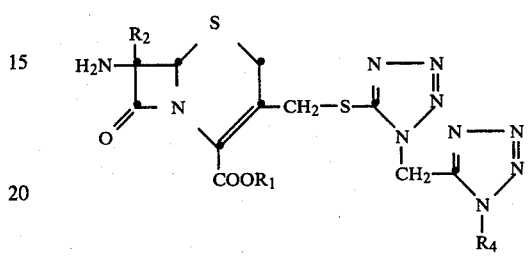

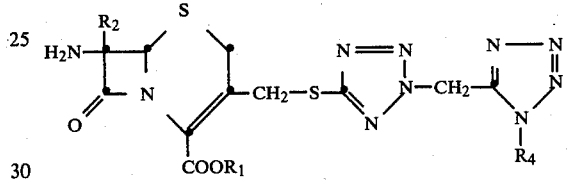

wherein R₁, R₂, and R₄ have the same meanings as defined above.

The N-acylation of the above 7-amino nucleus compounds can be carried out by a wide variety of acylation methods commonly employed in the cephalosporin art. For example, the acylation can be carried out under non-aqueous conditions or under aqueous conditions. Under the former conditions, an organic soluble active derivative of the carboxylic acid used to form the desired acyl group is formed and used to acylate the 7-amino nucleus compound. Examples of active derivatives of the carboxylic acid which can be formed include the active esters, for example those formed with hydroxybenzotriazole, or N-hydroxysuccinimide; mixed anhydrides formed with the carboxylic acid and methyl chloroformate or isobutyl chloroformate; and acid azides. The free acids themselves can be employed when used in the presence of a condensing agent such as EEDQ. Acylation can also be carried out under aqueous conditions, for example by employing an acid halide, for example acid chloride or acid bromide in an aqueous organic medium containing a hydrogen halide acceptor, for example a tertiary alkyl amine such as triethylamine or pyridine or, alternatively, a base such as sodium bicarbonate or sodium carbonate. In general, higher yields are obtained in acylations carried out under non-aqueous conditions.

The 7-amino-3-(bis-tetrazolmethyl) nucleus compounds of the above formulas are prepared with 7-aminocephalosporanic acid (7-ACA). In preparing these nucleus compounds, 7-aminocephalosporanic acid or an ester thereof is reacted with the 1-(1H-tetrazol-5-ylmethyl)-1H-tetrazol-5-thiol or the 2-(1H-tetrazol-5-ylmethyl)-2H-tetrazol-5-thiol to form the compounds of the above formulas. The reaction, which results in the replacement of the acetoxy group in the 3-position of 7-ACA with the bis-tetrazolmethyl thiol, can be carried out under non-aqueous conditions when in the above formulas $R_1$ is hydrogen or an ester, and under aqueous conditions when $R_1$ is hydrogen.

The preparation of the nucleus compounds represented by the above formula is carried out under non-aqueous conditions as follows. 7-Aminocephalosporanic acid is reacted with the bis-tetrazolmethyl thiol at a temperature between about 25° C. to about 80° C. in glacial acetic acid in the presence of boron trifluoride etherate. The reaction proceeds at a convenient rate at a temperature of about 60°–80° C. and higher yields are obtained when an excess of the thiol is employed. Following the reaction, the mixture is diluted with water and the pH is adjusted to the isoelectric point of the substituted nucleus free acid. At the isoelectric point of about pH 4.0–5.0, the product precipitates from the reaction mixture.

The displacement under aqueous conditions is carried out as follows. An aqueous solution of 7-ACA at a basic pH of about pH 7.5–8.5 is mixed with a solution of the bis-tetrazolmethyl thiol, in the form of the sodium or potassium salt, and the reaction mixture is stirred with mild heating. The reaction product mixture is acidified with a mineral acid such as hydrochloric acid to the isoelectric point. The 3-substituted 7-amino free acid compound precipitates from the reaction mixture and is recovered by filtration. The substituted nucleus compound can be purified if necessary by recrystallization from a suitable solvent or, alternatively, via a salt form thereof such as the hydrochloride salt or the tosylate salt.

The 3-substituted 7-amino nucleus compounds represented by the above formulas are valuable intermediates useful in the preparation of the antibiotic compounds of this invention. As mentioned above, the 7-amino group of the nucleus compound can be acylated with the desired carboxylic acid and preferably an active derivative thereof. The N-acylation of the above 7-amino substituted nucleus compounds is a coupling reaction of a carboxylic acid and an amino compound and can be carried out by acylation methods employed in the acylation of the 7-aminocephalosporin nucleus compound, for example, 7-ACA and 7-ADCA. To illustrate these acylation methods in the preparation of the compounds of this invention, the following paragraphs describe various acylation methods which are used in the preparation of the compounds of the invention.

Aqueous Acylation

The compounds of the above formulas 2 and 3 can be acylated under aqueous conditions under essentially Schotten-Bauman conditions, for example, an acid halide such as the acid chloride is reacted in aqueous acetone with the 3-substituted 7-amino nucleus compound in the form of a salt in the presence of a hydrogen halide accepting base. The base can be an inorganic base such as sodium or potassium carbonate or bicarbonate or a tertiary amine such as pyridine or a trialkylamine, such as trimethylamine or triethylamine. The acylation is generally carried out at room temperature and the product is readily recovered. For example, when a salt form of the 7-amino nucleus compound is employed the reaction mixture is acidified to convert the N-acylated nucleus to the free acid which is extracted with a water immiscible organic solvent.

The acyl chlorides used in the acylation are best prepared by reacting the free acid with oxalyl chloride in an inert organic solvent in the presence of a hydrogen chloride acceptor such as propylene oxide. Preferably, the oxalyl chloride is reacted with the acid in the organic solvent in the presence of a catalytic amount of dimethylformamide. Solvents such as THF and acetonitrile are suitable.

Examples of acid chlorides which can be used to acylate the 3-substituted 7-amino nucleus compounds (Formula 1, R=H) to provide the antibiotics of the Formula 1 are acetyl chloride, cyanoacetyl chloride, chloroacetyl chloride, propionyl chloride, benzoyl chloride, phenylacetyl chloride, p-chlorophenylacetyl chloride, p-hydroxyphenylacetyl chloride, p-methoxyphenylacetyl chloride, o-aminomethylphenylacetyl chloride hydrochloride, phenoxyacetyl chloride, p-chlorophenoxyacetyl chloride, p-methoxyphenoxyacetyl chloride, phenylmercaptoacetyl chloride, 3,5-dichlorophenylmercaptoacetyl chloride, p-fluorophenylmercaptoacetyl chloride, thiophene-2-acetyl chloride, thiophene-3-acetyl chloride, furan-2-acetyl chloride, 1H-tetrazole-1-ylacetyl chloride, 1H-tetrazole-5-ylacetyl chloride, mandeloyl chloride, o-formylmandeloyl chloride, α-(p-nitrobenzyloxycarbonyl)-phenylacetyl chloride, α-sulfophenylacetyl chloride and, α-(diphenylmethyloxycarbonyl)-2-thienylacetyl chloride.

In an example of the aqueous acylation a solution of 7-amino-3-[1-(1H-tetrazole-5-ylmethyl)-1H-tetrazole-5-ylthiomethyl]-3-cephem-4-carboxylic acid (formula 2, $R_1=R_2=R_4=H$) in aqueous acetone containing a slight excess of sodium carbonate is treated with stirring at a temperature between about −5° C. and 35° C. with a solution of a slight molar excess of thiophene-2-acetyl chloride in acetone. The acylation product, 7-(2-thienylacetamido)-3-[1-(1H-tetrazole-5-ylmethyl)1H-tetrazole-5-ylthiomethyl]-3-cephem-4-carboxylic acid represented by the following formula is obtained.

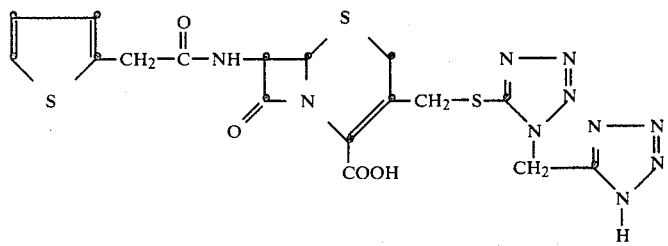

The 3-substituted 7-amino nucleus compounds can also be acylated under aqueous conditions with active esters of carboxylic acids formed with hydroxybenzotriazole or hydroxysuccinimide. For example, syn 7β-[α-methoximino-α-(2-amino-1,3-thiazol-4-yl)-acetamido]-3-[2-(1H-tetrazole-5-ylmethyl)-2H-tetrazol-5-ylthiomethyl]-3-cephem-4-carboxylic acid is prepared by acylating 7-amino-3-[2-(1H-tetrazole-5-ylmethyl)-

2H-tetrazol-5-ylthiomethyl]-3-cephem-4-carboxylic acid of the formula

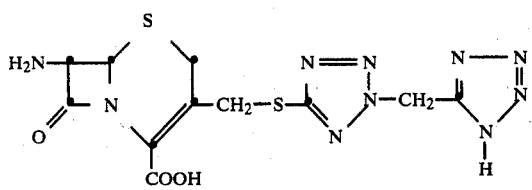

with α-methoximino-α-(2-amino-1,3-thiazol-4-yl)acetic acid hydroxybenzotriazole ester of the formula

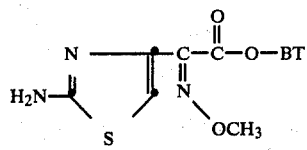

wherein BT=benzotriazol-1-yl

The acylation is carried out in aqueous acetone at a pH of about 7-8.

Non-Aqueous Acylation

The acylation of the 3-substituted 7-amino nucleus compounds is carried out under non-aqueous conditions with an active derivative of the carboxylic acid. Generally, the carboxy group of the nucleus is protected during the acylation, for example, with a carboxylic acid protecting group. Suitable protecting groups include, for example, p-nitrobenzyl, p-methoxybenzyl, benzyl, diphenylmethyl, 2,2,2-trichloroethyl, t-butyl, and like ester groups which are easily cleaved under hydrolytic or hydrogenolytic conditions. Alternatively, the carboxy group of the 7-amino nucleus compound can be temporarily protected during the N-acylation as a silyl ester, for example, the trimethylsilyl ester formed by reacting a suspension of the free nucleus acid with a silylating agent such as trimethylsilyl acetamide or bis-trimethylsilyl acetamide.

Active derivatives of the carboxylic acid acyl moiety which can be employed in the acylation include, for example, the pentachlorophenyl ester, a mixed anhydride, for example, the mixed anhydride formed with methyl chloroformate or with isobutyl chloroformate; an active ester formed with N-hydroxysuccinimide or hydroxybenzotriazole (HBT); an acid halide or an acid azide.

The free acid itself can be coupled with the 7-amino nucleus compound in the presence of a condensing agent, for example, a carbodiimide such as dicyclohexylcarbodiimide.

The following illustrate the non-aqueous acylation method for the preparation of compounds of the formula 1.

7-Amino-3-[1-(1H-tetrazol-5-yl-methyl)-1H-tetrazol-5-ylthiomethyl]-3-cephem-4-carboxylic acid is reacted in acetonitrile with trimethylsilyl acetamide to form the trimethylsilyl ester of the 7-amino nucleus, and the nucleus ester is acylated with the mixed anhydride of an amino-protected phenylglycine formed with methyl chloroformate to provide the amino-protected 7-phenylacetamido-3-[1-(1H-tetrazol-5-ylmethyl)-1H-tetrazol-5-ylthiomethyl]-3-cephem-4-carboxylic acid trimethylsilyl ester. The trimethylsilyl ester is hydrolyzed to the free acid and the amino protecting group is removed to provide the deprotected amino acid. The above is illustrated by the following reaction scheme wherein the t-butyloxycarbonyl group is the amino protecting group.

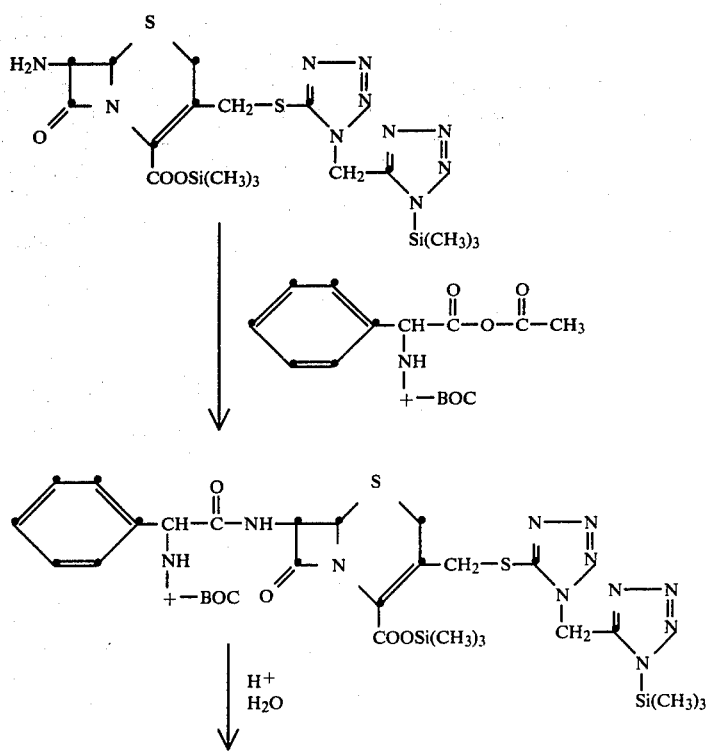

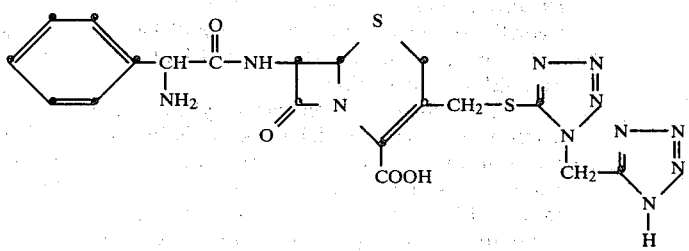

The t-butyloxycarbonyl group (t-BOC) and the trimethylsilyl ester group are removed upon treatment of the protected intermediate under acid hydrolysis conditions.

Syn 7β-[α-Methoximino-α-(2-amino-1,3-thiazol-4-yl)acetamido]-3-[2-(1H-tetrazol-5-ylmethyl)-2H-tetrazol-5-ylthiomethyl]-3-cephem-4-carboxylic acid is prepared by acylating 7-amino-3-[2-(1H-tetrazol-5-ylmethyl)-2H-tetrazol-5-ylthiomethyl]-3-cephem-4-carboxylic acid trimethylsilyl ester with the hydroxybenzotriazole ester of α-methoximino-α-(2-amino-1,3-triazol-4-yl)acetic acid in a dry solvent such as tetrahydrofuran or acetonitrile. The product is recovered from the reaction mixture by extraction following acid hydrolysis of the trimethylsilyl ester group and is purified by reversed phase silica gel HPLC.

The compounds represented by the formula 1, wherein R is an acyl group represented by the formula

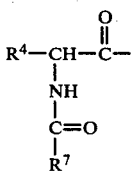

wherein $R^7$ is hydroxyphenyl or hydroxypyridyl, are prepared by acylating the α-amino group of a 7-phenylglycyl, thienylglycyl, or furylglycyl substituted cephalosporin represented by the formula 1 wherein R is an acyl group of the formula

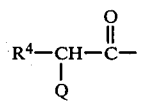

wherein Q is amino, with an active ester of the hydroxy substituted benzoic acid or the hydroxy substituted pyridine carboxylic acid. Preferably, the acylation is carried out by first preparing the hydroxybenzotriazole ester of the acid in the presence of a condensing agent such as a carbodiimide, for example, dicyclohexyl carbodiimide. The acylation of the phenylglycyl substituted cephalosporin of the formula 1 is carried out under non-aqueous conditions, for example, in dry THF or acetonitrile.

Representative of the hydroxy substituted benzoic acids and the hydroxy substituted pyridine carboxylic acids which can be employed are 4-hydroxybenzoic acid, 3-hydroxybenzoic acid, 2-hydroxybenzoic acid, 2,3-dihydroxybenzoic acid, 2,6-dihydroxybenzoic acid, and 3,4-dihydroxybenzoic acid, 3-hydroxypyridine-4-carboxylic acid, 2,3-dihydroxypyridine-4-carboxylic acid, 4-hydroxypyridine-3-carboxylic acid, 2,4-dihydroxypyridine-3-carboxylic acid, and 4,5-dihydroxypyridine-3-carboxylic acid.

An example of the preparation of the above hydroxy-substituted benzoic and hydroxy-substituted pyridine carboxylic acid derivatives is illustrated in the following reaction scheme in which 7-phenylglycylamido-3-[1-(1H-tetrazol-5-ylmethyl)-1H-tetrazol-5-ylthiomethyl]-3-cephem-4-carboxylic acid is reacted in acetonitrile with 2-hydroxybenzoic acid hydroxybenzotriazole ester to provide 7-[α-(2-hydroxybenzamido)-phenylacetamido]-3-[1-(1H-tetrazol-5-ylmethyl)-1H-tetrazol-5-ylthiomethyl]-3-cephem-4-carboxylic acid.

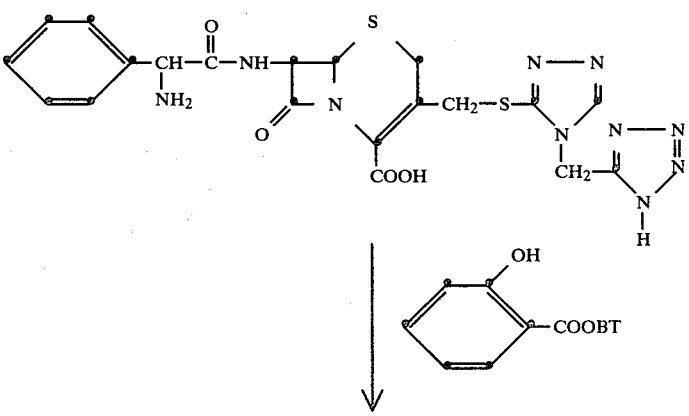

-continued

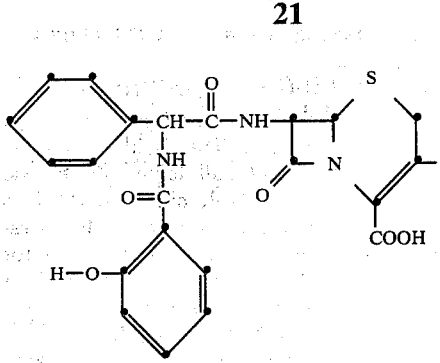

The compounds represented by the formula 1 wherein $R_7$ is a group of the formula

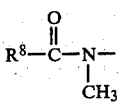

are prepared with a compound of the formula 1 wherein R is a phenylglycyl, furylglycyl, or thienylglycyl group represented by the term $R^4$—CH(Q)—C=O— wherein Q is amino. When in the above formula $R^8$ is phenyl, chlorophenyl, furyl, styryl, nitrostyryl, or chlorostyryl, the compounds are prepared by acylating the α-amino group of the phenylglycyl substituted cephalosporin with an N-chlorocarbonyl amide derivative represented by the following formula.

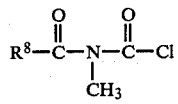

The N-chlorocarbonyl amides are prepared by reacting the N-methyl amide of the $R^8$-COOH acid with phosgene in an inert solvent in the presence of a hydrogen halide acceptor. Representative of the N-methyl amides which can be employed in the acylation are N-methylbenzamide, N-methyl-4-chlorobenzamide, N-methyl-3-chlorobenzamide, N-methyl-2-furoic acid amide, N-methyl-3-furoic acid amide, N-methylcinnamide, N-methyl-4-chlorocinnamide, N-methyl-4-nitrocinnamide, N-methyl-2-chlorocinnamide, and N-methyl-2-nitrocinnamide.

The N-methyl amide is reacted with phosgene in an inert solvent such as a chlorinated hydrocarbon solvent, for example, methylene chloride or trichloroethane in the presence of a hydrogen halide acceptor, for example, a tri-lower alkyl amine, for example, triethylamine or pyridine.

The N-chlorocarbonyl amides are coupled with the α-amino group of the cephalosporin compound via an N-acylation which can be carried out under aqueous or non-aqueous conditions in the presence of a hydrogen halide acceptor. The acylation is carried out at a temperature between about $-5°$ C. and about 35° C. and preferably at about 0°–5° C. The solvents which can be employed in the acylation includes acetonitrile, THF, DMF, and dimethylacetamide. In an example of the acylation, 7-phenylglycylamido-3-[1-(1-methyl-1H-tetrazol-5-ylmethyl)-1H-tetrazol-5-ylthiomethyl]-3-cephem-4-carboxylic acid is converted to the trimethylsilyl ester in acetonitrile with trimethylsilyl acetamide, and the ester is reacted with N-chlorocarbonyl-N-methyl-2-chlorobenzamide at a temperature of about 20° C. to provide the compound of the formula 1, 7-[α-(N-methyl-2-chlorobenzamido)phenylacetamido]-3-[1-(1-methyl-1H-tetrazol-5-ylmethyl)-1H-tetrazol-5-ylthiomethyl]-3-cephem-4-carboxylic acid trimethylsilyl ester. The ester is hydrolyzed with mild acid hydrolysis following the acylation and the free acid is recovered by extraction from the reaction mixture.

The compounds represented by the formula 1 wherein $R^8$ is a $C_1$–$C_4$ alkylamino group are likewise prepared by the acylation of the α-amino substituted cephalosporin represented by the formula 1 with an N-alkyl-N'-methyl-N'-chlorocarbonyl substituted urea. For example, N,N'-dimethylurea is reacted with phosgene in an inert solvent to provide the N-chlorocarbonyl derivative which is then used in the acylation of the α-amino substituted cephalosporin under the acylation conditions described above. Representative of the N,N'-disubstituted ureas which can be used in the acylation to prepare compounds of the formula 1 are N,N'-dimethylurea, N-ethyl, N'-methylurea, N-(n-butyl)-N'-methylurea and like N-($C_1$–$C_4$ alkyl-N'-methylureas.

The compounds represented by the formula 1 wherein $R_2$ is methoxy are prepared either by the acylation of the corresponding 7-amino-7-methoxy compound (R=hydrogen), or by the replacement of the 3-acetoxy group of a 7-acylamino-7-methoxycephalosporanic acid, or by the replacement of a 3' halo group of a 7-acylamino-7-methoxy-3-halomethyl-3-cephem-4-carboxylic acid ester.

Acylations of the 7-amino-7-methoxy 3-substituted nucleus compounds are carried out with nucleus in an esterified form, and preferably under non-aqueous acylation conditions. The non-aqueous acylation conditions described hereinabove are suitable acylation methods for the 7-methoxy nucleus esters.

Alternatively, a 7-acylamino-7-methoxy-3-acetoxymethyl-3-cephem-4-carboxylic acid can be reacted with a bis-tetrazolmethyl thiol to prepare a compound of the invention by following the reaction procedures described above for the non-methoxylated cephalosporin compounds.

In yet another alternative for preparing the 7-methoxycephalosporin compounds of the formula 1, a 7-acylamino-7-methoxy-3-bromomethyl-3-cephem-4-carboxylic acid ester is reacted with a bis-tetrazolmethyl thiol to provide the compound of the invention. For example, p-nitrobenzyl 7-(2-thienylacetamido)-7-methoxy-3-bromomethyl-3-cephem-4-carboxylate is reacted in dimethylformamide with a molar excess of 1-(1H-tetrazol-5-ylmethyl)-1H-tetrazol-5-thiol at room temperature to provide p-nitrobenzyl 7-(2-thienylacetamido)-7-methoxy-3-[1-(1H-tetrazol-5-ylmethyl)-1H-tetrazol-5-ylthiomethyl]-3-cephem-4-carboxylate. Deesterification of the p-nitrobenzyl ester group provides the compound of the formula 1 wherein $R_1$ is hydrogen. The deesterification of the p-nitrobenzyl ester group is carried out by known reductive cleavage procedures, for example, by catalytic hydrogenolysis over 5% palladium on carbon in an inert solvent such as tetrahydrofuran or acetonitrile, or by electrolytic reductive cleavage at a mercury pool cathode.

Other readily removed carboxylic acid protecting ester groups can likewise be used in the preparation of the 7-methoxy substituted cephalosporins of the invention. For example, well known carboxylic acid protecting groups in the art include the diphenylmethyl ester group and the p-methoxybenzyl group, both of which can be removed by treating the ester with trifluoroacetic acid in the presence of anisole preferably at a temperature of about 0° C. to about 10° C. Other ester groups such as haloalkyl groups, for example, the 2,2,2-trichloroethyl group and the 2-iodoethyl group can also be employed and are removed by reduction with zinc removed from the thiol by electrolytic reduction at a mercury pool cathode.

Alternatively, the 1-[1-($C_1$-$C_3$ alkyl)-1H-tetrazol-5-ylmethyl]-1H-tetrazol-5-thiol is prepared with ethyl 5-chloro-1H-tetrazol-1-acetate. The 5-chlorotetrazole acetate is reacted with a $C_1$-$C_3$ alkylamine to provide the corresponding N-($C_1$-$C_3$ alkyl)amide. The amide is then reacted with an excess of phosgene at a temperature of about $-5°$ to about 10° C. in an inert solvent, for example, a halogenated hydrocarbon solvent, such as methylene chloride or dichloroethane, to provide the corresponding N-chlorocarbonyl-N-($C_1$-$C_3$ alkyl)amide. The N-chlorocarbonylamide is then reacted with tetramethylguanidinium azide in dioxane at the reflux temperature to provide the 1-[1-($C_1$-$C_3$ alkyl)-1H-tetrazol-5-ylmethyl]-5-chloro-1H-tetrazole. The latter is then reacted with sodium hydrosulfide to replace the 5-chloro group with the thiol group.

A preferred group of compounds of this invention are represented by the following general formula.

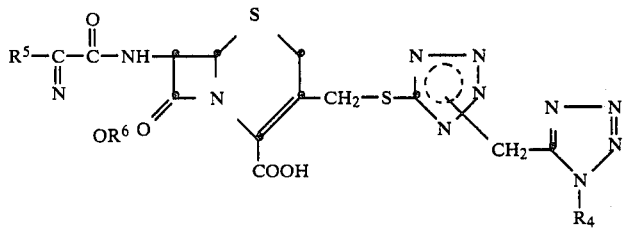

and an acid.

The bis-tetrazolmethyl thiol compounds used in the preparation of the compounds of the invention are prepared as described in copending application Ser. No. 187,861, filed September 17, 1980, filed this even date. As described therein, 1-cyanomethyl-1H-tetrazol-5-ylthiol is reacted with tetramethylguanidinium azide is dioxane at the reflux temperature to provide the 1-(1H-tetrazol-5-ylmethyl)-1H-tetrazol-5-thiol. The corresponding 2H-tetrazole substituted tetrazole is obtained by alkylating 1H-tetrazole-5-thiol, wherein the thiol group is protected with a thiol protecting group such as the benzyl group, with a haloaceonitrile such as chloroacetonitrile in the presence of a base such as potassium or sodium hydroxide. The alkylation provides a mixture of 1- and 2-cyanomethyl-5-benzylthio-1H-tetrazole. The isomeric mixture of the cyanomethyl substituted tetrazole is then reacted with tetramethylguanidinium azide or with aluminum triazide at elevated temperatures to provide a mixture of 1-(1H-tetrazol-5-ylmethyl)-1H-tetrazol-5-thiol and 2-(1H-tetrazol-5-ylmethyl)-2H-tetrazol-5-thiol wherein the thiol group is protected, for example, with a benzyl group. The isomeric mixture of the bis-tetrazoles is separated into the individual isomers via HPLC chromatography on silica gel.

The $C_1$-$C_3$ alkyl substituted tetrazoles ($R_4$=$C_1$-$C_3$ alkyl) are obtained by alkylating the respective S-protected isomeric tetrazoles with a $C_1$-$C_3$ alkyl bromide or iodide in the presence of a base. The alkylation affords an isomeric mixture which can be separated into the individual isomers by HPLC chromatography. Following the separation of the individual isomeric tetrazoles or the alkylation products thereof as described above, the S-protecting group eg. the benzyl group is wherein $R^5$ is a group represented by the formula

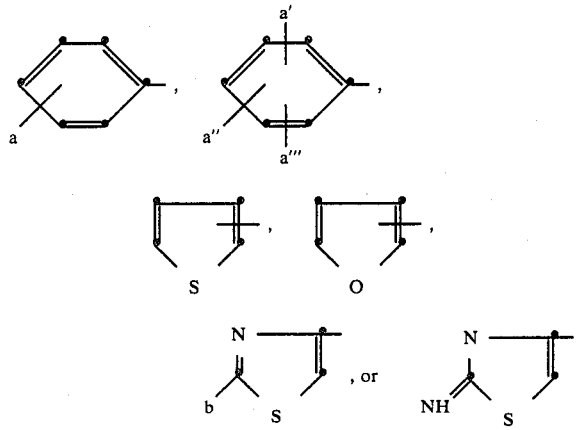

wherein a, a', a'', a''', b, $R_4$ and $R^6$ have the same meanings as defined above.

Compounds of the above formula which are especially preferred are represented by the formula when $R^6$ is $C_1$-$C_3$ alkyl and $R_4$ is hydrogen. Especially preferred compounds are those represented by the formula when $R^5$ is 2-furyl or the 2-amino-1,3-thiazol-4-yl group or the tautomeric 2-imino form thereof as shown by the above structural formula. As is known in the art, the oximino function in the side chain can have either the syn or anti form and the compounds in the syn form are preferred owing to their enhanced activity over the compounds in the anti form. Examples of the above compounds include the following.

syn 7β-[α-hydroxyimino-α-(2-furyl)acetamido]-3-[1-(1H-tetrazol-5-ylmethyl)-1H-tetrazol-5-ylthiomethyl]-3-cephem-4-carboxylic acid, syn 7β-[α-hydroxyimino-α-(2-amino-1,3-thiazol-4-yl)-acetamido]-3-[1-(1H-tetrazol-5-ylmethyl)-1H-tetrazol-5-ylthiomethyl]-3-cephem-4-carboxylic acid, syn 7β-[α-methoximino-α-(2-amino-1,3-thiazol-4-yl)-acetamido]-3-[1-(1H-tetrazol-5-ylmethyl)-1H-tetrazol-5-ylthiomethyl]-3-cephem-4-carboxylic acid, syn 7β-[α-methoximino-α-(2-amino-1,3-thiazol-4-yl)-acetamido]-3-[1-methyl-1H-tetrazol-5-ylmethyl)-1H-tetrazol-5-ylthiomethyl]-3-cephem-4-carboxylic acid, syn 7β-[α-hydroxyimino-α-(2-amino-1,3-thiazol-4-yl)-acetamido]-3-[1-(1H-tetrazol-5-ylmethyl)-1H-tetrazol-5-ylthiomethyl]-3-cephem-4-carboxylic acid, syn 7β-[α-methoximino-α-(2-amino-1,3-thiazol-4-yl)-acetamido]-3-[2-(1H-tetrazol-5-ylmethyl)-2H-tetrazol-5-ylthiomethyl]-3-cephem-4-carboxylic acid, 7β-(D-α-carboxyphenylacetamido)-3-[1-(1H-tetrazol-5-ylmethyl)-1H-tetrazol-5-ylthiomethyl]-3-cephem-4-carboxylic acid, 7β-(D-α-sulfophenylacetamido)-3-[1-(1-methyl-1H-tetrazol-5-ylmethyl)-1H-tetrazol-5-ylthiomethyl]-3-cephem-4-carboxylic acid, 7β-[α-amino-(2-thienyl)acetamido]-3-[2-(1H-tetrazol-5-ylmethyl)-2H-tetrazol-5-ylthiomethyl]-3-cephem-4-carboxylic acid, 7β-[α-(2,3-dihydroxybenzamido)phenylacetamido]-3-[1-(1H-tetrazol-5-ylmethyl)-1H-tetrazol-5-ylthiomethyl]-3-cephem-4-carboxylic acid, 7β-[α-(2-hydroxypyridin-1-ylcarbonylamino)-phenylacetamido]-3-[1-(1H-tetrazol-5-ylmethyl)-1H-tetrazol-5-ylthiomethyl]-3-cephem-4-carboxylic acid, and the α-substituted-aminophenylacetamido compounds represented by the formula

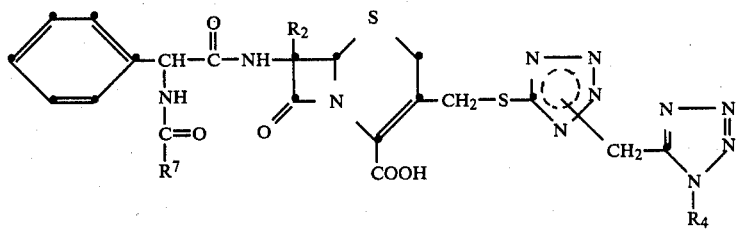

and the pharmaceutically acceptable non-toxic salts thereof.

Illustrative of other compounds of the invention represented by formula 1 are the following:

7β-benzamido-3-[1-(1H-tetrazol-5-ylmethyl)-1H-tetrazol-5-ylthiomethyl]-3-cephem-4-carboxylic acid, 7β-phenylacetamido-3[1-(1H-tetrazol-5-ylmethyl)-1H-tetrazol-5-ylthiomethyl]-3-cephem-4-carboxylic acid, 7β-phenoxyacetamido-3-[1-(1-methyl-1H-tetrazol-5-ylmethyl)-1H-tetrazol-5-ylthiomethyl]-3-cephem-4-carboxylic acid, 7β-phenoxyacetamido-7α-methoxy-3-[1-(1H-tetrazol-5-yl)-1H-tetrazol-5-ylthiomethyl]-3-cephem-4-carboxylic acid, 7β-phenoxyacetamido-3-[2-(1H-tetrazol-5-ylmethyl)-2H-tetrazol-5-ylthiomethyl]-3-cephem-4-carboxylic acid, 7β-(2-thienylacetamido)-3-[1-(1H-tetrazol-5-ylmethyl)-1H-tetrazol-5-ylthiomethyl]-3-cephem-4-carboxylic acid, 7β-(2-thienylacetamido)-7α-methoxy-3-[1-(1-ethyl-1H-tetrazol-5-ylmethyl)-1H-tetrazol-5-ylthiomethyl]-3-cephem-4-carboxylic acid, 7β-phenylmercaptoacetamido-3-[1-(1H-tetrazol-5-ylmethyl)-1H-tetrazol-5-ylthiomethyl]-3-cephem-4-carboxylic acid, 7β-(D-phenylglycylamido)-3-[1-(1-methyl-1H-tetrazol-5-ylmethyl)-1H-tetrazol-5-ylthiomethyl]-3-cephem-4-carboxylic acid, 7β-(D-mandelamido)-7α-methoxy-3-[1-(1H-tetrazol-5-ylmethyl)-1H-tetrazol-5-ylthiomethyl]-3-cephem-4-carboxylic acid, wherein $R^7$ is a group of the formulae

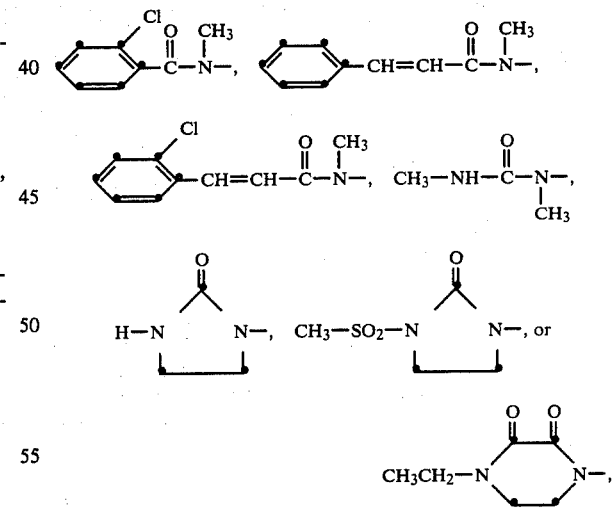

and the pharmaceutically acceptable salts thereof.

The bis-tetrazol-thiomethyl substituted cephalosporins of this invention are broad spectrum antibiotics which inhibit the growth of both gram positive and gram negative microorganisms which are pathogenic to man and animals. The antibacterial activity of these compounds was demonstrated in in vitro tests carried out by the agar dilution method. The following Table 2 lists the minimum inhibitory concentrations of representative compounds of the invention.

TABLE 2

In Vitro ANTIBACTERIAL ACTIVITY OF bis-TETRAZOLEMETHYL CEPHALOSPORINS

Test Compound[1] Minimum Inhibitory Concentration (mcg/ml)

| Microorganism | Strain | A | B | C | D | E | F | G |
|---|---|---|---|---|---|---|---|---|
| Staphylococcus aureus | X1.1 | 2 | .5 | 1 | 4 | 4 | 2 | 4 |
| Staphylococcus aureus | V41 | 2 | 2 | 8 | 16 | 8 | 4 | 8 |
|  | X400 | 16 | 32 | 128 | >128 | >128 | >128 | >128 |
|  | S13E | 8 | 4 | 16 | 32 | 16 | 8 | 32 |
| Staphylococcus epidermidis | EPI1 | 16 | 4 | 8 | 8 | 16 | 8 | 32 |
| Staphylococcus epidermidis | EPI2 | 8 | 4 | 32 | 32 | 64 | 32 | 64 |
| Streptococcus Group A | C203 | .5 | 1 | .5 | .5 | .06 | .03 | .03 |
| Streptococcus pneumoniae | PARK | 4 | 2 | .25 | .25 | .03 | .015 | .03 |
| Streptococcus Group D | X66 | 64 | 128 | >128 | 128 | >128 | >128 | >128 |
| Streptococcus Group D | 9960 | >128 | 64 | 128 | 64 | 16 | 16 | >128 |
| Haemophilus influenzae | Brun[2] | — | — | 4 | .015 | .125 | .125 | .06 |
| Haemophilus influenzae | 251[3] | — | — | 4 | .015 | .125 | .125 | .06 |
| Haemophilus influenzae | C.L.[2] | .25 | 1 | — | — | — | — | — |
| Haemophilus influenzae | 76[3] | .25 | .5 | — | — | — | — | — |
| Shigella sonnei | N9 | 8 | 4 | 1 | .25 | .125 | .125 | 2 |
| Escherichia coli | N10 | 8 | 4 | 2 | 2 | .25 | .25 | .25 |
| Escherichia coli | EC14 | 4 | 2 | .25 | .125 | .06 | .06 | .125 |
| Escherichia coli | TEM | 4 | 8 | 8 | 16 | .125 | .125 | .125 |
| Klebsiella sp. | X26 | 1 | .5 | 2 | 1 | .06 | .06 | .125 |
| Klebsiella sp. | KAE | 4 | >128 | >128 | >128 | 16 | 4 | 8 |
| Enterobacter aerogenes | X68 | 4 | .5 | .25 | .25 | .06 | .125 | .06 |
| Enterobacter aerogenes | C32 | >128 | 32 | 4 | 2 | .25 | .125 | .25 |
| Enterobacter aerogenes | EB17 | >128 | 16 | 2 | .5 | .25 | .25 | .25 |
| Enterobacter cloacae | EB5 | >128 | >128 | 128 | 2 | 2 | 1 | 2 |
| Enterobacter cloacae | 265A | >128 | >128 | >128 | 128 | 64 | 32 | 64 |
| Salmonella sp. | X514 | 1 | .5 | 1 | 2 | .125 | .25 | .125 |
| Salmonella sp. | 1335 | 2 | 1 | 2 | 4 | .25 | .5 | .5 |
| Pseudomonas aeruginosa | X528 | >128 | >128 | >128 | 8 | 8 | 32 | 16 |
| Pseudomonas aeruginosa | X239 | >128 | >128 | >128 | 4 | 16 | 32 | 16 |
| Pseudomonas aeruginosa | Ps18 | >128 | >128 | >128 | 8 | 8 | 32 | 32 |
| Serratia marcescens | X93 | 16 | >128 | 32 | 1 | .25 | .125 | .25 |
| Serratia marcescens | SE3 | 64 | >128 | >128 | 4 | 1 | .5 | 2 |
| Proteus morganii | PR15 | 64 | 64 | 2 | 1 | .06 | .125 | .5 |
| Proteus inconstans | PR33 | 4 | 64 | 2 | 2 | .125 | .5 | 1 |
| Proteus rettgeri | PR7 | 4 | 4 | 4 | 4 | .125 | .03 | .03 |
| Proteus rettgeri | C24 | 1 | 8 | .5 | 8 | .125 | .25 | 2 |
| Citrobacter freundii | CF17 | >128 | >128 | >128 | 32 | 32 | 16 | 64 |
| Bordetella bronchoseptica |  | 16 | >128 | 8 | 16 | 32 | 32 | 128 | 64 |

[1]A. 7β-(2-Thienylacetamido)-7α-methoxy-3-[1-(1H-tetrazol-5-ylmethyl)-1H-tetrazol-5-ylthiomethyl]-3-cephem-4-carboxylic acid
B. 7β-(2-Thienylacetamido)-3-[1-(1-methyl-1H-tetrazol-5-ylmethyl)-1H-tetrazol-5-ylthiomethyl]-3-cephem-4-carboxylic acid
C. 7β-(D o-Formylmandelamido)-3-[1-(1H-tetrazol-5-ylmethyl)-1H-tetrazol-5-ylthiomethyl]-3-cephem-4-carboxylic acid
D. 7β-[D α-(4-Ethylpiperazin-2,3-dione-1-ylcarbonyl-amino)-α-(4-hydroxyphenyl)acetamido]-3-[1H-tetrazol-5-ylmethyl)-1H-tetrazol-5-ylthiomethyl]-3-cephem-4-carboxylic acid
E. syn 7β-[α-Methoximino-α-(2-amino-1,3-thiazol-4-yl)-acetamido]-3-[1-(1H-tetrazol-5-ylmethyl)-1H-tetrazol-5-ylthiomethyl]-3-cephem-4-carboxylic acid
F. syn 7β-[α-Methoximino-α-(2-amino-1,3-thiazol-4-yl)-acetamido]-3-[1-(1-methyl-1H-tetrazol-5-ylmethyl)-1H-tetrazol-5-ylthiomethyl]-3-cephem-4-carboxylic acid
G. syn 7β-[α-Methoximino-α-(2-amino-1,3-thiazol-4-yl)-acetamido]-3-[2-(1H-tetrazol-5-ylmethyl)-2H-tetrazol-5-ylthiomethyl]-3-cephem-4-carboxylic acid.
[2]H. influenzae sensitive strain
[3]H. influenzae resistant strain The data in TABLE 2 were obtained in the agar dilution test method using Mueller-Hinton agar containing two percent Supplement C (Difco). Serial two-fold dilutions were run with the highest concentration on test at 128 mcg/ml.

Compound E (TABLE 2), a preferred compound of the invention, was administered to mice infected with various pathogens to determine the compound's effective dose (ED$_{50}$). Listed below in TABLE 3 are the ED$_{50}$ values determined with the indicated infectious organism.

TABLE 3

In Vivo ACTIVITY OF COMPOUND E IN MICE

| Bacteria (strain) | ED$_{50}$ (mg/kg × 2) s.c.[1] |
|---|---|
| Escherichia coli (EC14) | 0.16 |
| Proteus vulgaris (PV2S) | 0.12 |
| Serratia marcescens (SE3) | 1.0 |
| Staphylococcus aureus (3055) | 7.6 |
| Streptococcus pyogenes (C203) | 0.21 |

[1]Subcutaneous doses at 1 and 5 hours post infection

Compound E was also effective in the treatment of ampicillin-resistant Haemophilus influenzae meningitis in infant rats. Compound E was found to be present in effective levels in the cerebro-spinal fluid of rats administered 20 mg/kg. s.c. of the compound.

The compounds of this invention are effective in the treatment of infectious diseases in man and animals when administered by the parenteral route at an effective dose of between about 50 mg/kg and about 500 mg/kg. The compounds can be administered intramuscularly or intravenously in suitable formulations. For intramuscular preparations, a sterile formulation of a suitable salt form of the compound of the invention can be formulated as, for example, the sodium salt in a pharmaceutical diluent such as Water for Injection, physiological saline, or as a suspension in a suitable pharmaceutically acceptable oil base such as an ester of a long chain fatty acid such as ethyl oleate. For intravenous administration, a pharmaceutically acceptable salt form of a compound of the invention is formulated in a physiological fluid such as Ringer's solution, 5% dextrose, or other suitable physiological fluid. As is common in antibiotic therapy, the amount of antibiotic administered is in general dependent upon the severity of the infection, the sensitivity of the particular patient, and the type of microorganism or microorganisms involved in the infection. Usually the compounds are administered from 2 to 4 times daily until the infection is controlled. Accordingly, this invention also relates to a pharmaceutical formulation comprising a compound of the invention as represented by the formula 1 wherein $R_1$ is hydrogen or a pharmaceutically acceptable salt and a physiological carrier.

The following examples further illustrate the present invention. In the examples, HPLC means high performance liquid chromatography and, unless indicated otherwise, a Waters and Associates Model 500 (silica gel) column was employed. The nuclear magnetic resonance spectra (NMR) were obtained on a Varian Associates Model T-60 Spectrometer; a Jeol Model FX-90Q was used for 90 MHz spectra; and a Jeol Model PFT-100 Spectrometer was used for 100 MHz spectra. Trimethylsilane (TMS) was used as the standard in the NMR spectra. The abbreviations used in the recitation of the NMR spectra have the following meanings: s=singlet; q=quartet; m=multiplet; d=doublet; t=triplet.

In the examples, abbreviations are used for certain solvents as follows: THF=tetrahydrofuran; DMF=dimethylformamide; DMAC=dimethylacetamide; MSA=trimethylsilylacetamide; BSA=bis-trimethylsilylacetamide.

EXAMPLE 1

7-Amino-3-[1-(1-methyl-1H-tetrazol-5-ylmethyl)-1H-tetrazol-5-ylthiomethyl]-3-cephem-4-carboxylic acid.

A solution of 1.54 g. of 7-aminocephalosporanic acid and 1.0 g. (5 mmole) of 1-(1-methyl-1H-tetrazol-5-ylmethyl)-1H-tetrazol-5-thiol in 7.0 ml. of glacial acetic acid was heated in an oil bath to a temperature of about 65°–70° C. To the hot reaction mixture were added 3.6 ml. of boron trifluoride etherate, and the reaction mixture was heated at a temperature of 65°–70° C. for one hour with stirring. The reaction mixture was then cooled to room temperature and 10 ml. of water were added. The reaction mixture was stirred for 15 minutes after water addition, was filtered, and then chilled in an ice bath. The pH of the cold mixture was adjusted to pH 4.5 with concentrated ammonium hydroxide. The precipitate which formed was filtered, washed repeatedly with water, with acetone, and finally with diethyl ether. The off-white solid product was vacuum dried for one hour at 40° C. There was obtained 1.5 g. (80% yield) of the title compound.

The following analytical data were obtained for the product.

Elemental analysis calculated for $C_{12}H_{14}N_{10}O_3S_2$:
Theory: C, 35.12; H, 3.44; N, 34.13; S, 15.62;
Found: C, 35.62; H, 3.53; N, 31.63; S, 14.52.

IR (KBr) carbonyl absorption at 1800 cm$^{-1}$.
NMR (T-60, NaHCO$_3$/D$_2$O).

EXAMPLE 2

7β-[α-Methoximino-α-(2-amino-1,3-thiazol-4-yl)acetamido]-3-[1-(1-methyl-1H-thiazol-5-ylmethyl)-1H-tetrazol-5-ylthiomethyl]-3-cephem-4-carboxylic acid.

To a solution of 5.9 g. (15.6 mmole) of 7-amino-3-[1-(1-methyl-1H-tetrazol-5-ylmethyl)-1H-tetrazol-5-ylthiomethyl]-3-cephem-4-carboxylic acid in 60 ml. of acetone and 60 ml. of water were added 6.2 g. (17.0 mmole) of α-methoxyimino-α-(2-amino-1,3-triazol-5-yl) acetic acid hydroxybenzotriazole ester, and the pH of the solution was maintained at about 7.5 with a 45% potassium phosphate solution. The reaction mixture was stirred at room temperature for about 12 hours after which the reaction mixture was evaporated in vacuo to remove the acetone solvent. The aqueous residue (pH 7.0) was extracted twice with 100 ml. portions of ethyl acetate and was then filtered. The aqueous layer was chilled to a temperature of about 0° C., and the pH adjusted to 2.5 with 20% hydrochloric acid. The acylation product which formed as a precipitate was filtered and washed repeatedly with water. The product was vacuum dried at room temperature.

The product obtained above was purified by high performance liquid chromatography as follows. A solution of 7.0 g. of the compound in 200 ml. of 0.05 M ammonium acetate containing 0.3 ml. of ammonium hydroxide was placed on a Waters and Associates Model 500 HPLC and the chromatogram was run on $C_{18}$ reverse phase silica gel initially with a mixture of 12% acetonitrile:2% acetic acid:86% water, and then with the mixture 15% acetonitrile:2% acetic acid:83% water. Thirty-two, 250 ml. fractions were collected. The chromatogram was monitored via analytical HPLC. Fractions 15–22 were combined and concentrated in vacuo. The product precipitated from the concentrate and was filtered and washed with water. On drying, 1.4 g. of the product were obtained.

The following nuclear magnetic resonance spectrum of the purified product was obtained.

NMR (100 MHz, DMSO-d$_6$)δ3.65 (m, 2H, C-2 methylene), 3.85 (s, 3H, oxime methyl), 4.15 (s, 3H, N-methyl [tetrazol]), 4.35 (m, 2H, C-3' methylene), 5.13 (d, 1H, C-6 H), 5.76 (q, 1H, C-7 H), 6.1 (s, 2H, methylene), 6.74 (s, 1H, thiazol H), 7.20 (broad s, 2H, thiazole amino H), and 9.58 (d, 1H, amide H) ppm.

EXAMPLE 3

7-Amino-3-[1-(1H-tetrazol-5-ylmethyl)-1H-tetrazol-5-ylthiomethyl]-3-cephem-4-carboxylic acid.

A suspension of 5.3 g. (29 mmole) of 1-(1H-tetrazol-5-ylmethyl)-1H-tetrazol-5-thiol and 6.8 g. (25 mmole) of 7-aminocephalosporanic acid were suspended in 38 ml. of glacial acetic acid, and the suspension was heated at a temperature of about 62° to about 65° C. in an oil bath. To the hot suspension were added 16.6 ml. of boron trifluoride etherate (distilled) and a nearly complete solution was obtained. The mixture was heated for 1 hour at a temperature of about 60° to about 65° C. with stirring. The reaction mixture was cooled and stirred for 1 hour at room temperature and 45 ml. of water were added. The diluted reaction mixture was then cooled to 0° C. and the pH adjusted to pH 4.0 with concentrated ammonium hydroxide. The product precipitated and was washed with water, with acetone, diethyl ether, and was dried in a vacuum oven for 2 hours at a temperature of 50° C. There were obtained 8.0 g. of the product (88% yield) as a light beige powder.

NMR (T-60, sodium bicarbonate/D$_2$O) ppm.: 4.3 (m, 2H, C-3' methylene) and 5.9 (s, 2H, methylene bridging tetrazole rings) delta.

EXAMPLE 4

7β-[α-Methoximino-α-(2-amino-1,3-thiazol-4-yl)acetamido]-3-[1-(1H-tetrazol-5-ylmethyl)-1H-tetrazol-5-ylthiomethyl]-3-cephem-4-carboxylic acid.

To a solution of 7.5 g. (20.6 mmole) of the bis-tetrazolmethyl nucleus prepared as described in the preceding example in 75 ml. of water and 75 ml. of acetone were added 8.6 g. (23.5 mmole) of α-methoximino-α-(2-amino-1,3-thiazol-4-yl)acetic acid hydroxybenzotriazole ester. The acylation mixture was maintained at a pH of 7.5 with a 45% solution of potassium phosphate. The reaction mixture was stirred at room temperature for about 12 hours and evaporated in vacuo to remove the acetone solvent. The aqueous residue was filtered and cooled in an ice bath. The pH of the aqueous phase was adjusted to pH 2.4 with 20% hydrochloric acid. The product precipitated as a thick yellow precipitate, was filtered, washed repeatedly with water, and was air-dried. There were obtained 6.5 g. of the product as a light beige solid.

The product was purified by HPLC chromatography as follows. Approximately 12 g. of the crude product prepared as described above were dissolved in 100 ml. of water by adding a 45% aqueous solution of potassium phosphate until the pH reached 5.4. This solution was pumped through a Waters and Associates Model 500 HPLC column (silica gel) over a reversed phase cartridge using the following systems.

A. 8% Acetonitrile:2% acetic acid:90% water (4 liters)

B. 10% Acetonitrile:2% acetic acid:88% water (6 liters)

Forty, 250 ml. fractions were collected and the fractions were monitored by ultraviolet absorption. Fractions 11-22 were combined and lyophilized to 2.5 g of an amorphous white solid.

NMR (360 MHz, DMSOd$_6$): δ(ppm). 3.65 (m, 2H, C-2 methylene), 3.85 (s, 3H, oxime methyl, syn), 4.35 (m, 2H, C-3' methylene), 5.13 (d, 1H, C—6H), 5.80 (q, 1H, C—7H), 6.02 (m, 2H, methylene between tetrazole rings), 6.75 (s, 1H, thiazole ring H), 7.24 (broad s, 2H, thiazole amino), and 9.60 (d, 1H, 7—amide H).

EXAMPLE 5

7β-[α-Methoximino-α-(2-amino-1,3-thiazol-4-yl)acetamido]-3-[2-(1H-tetrazol-5-ylmethyl)-2H-tetrazol-5-ylthiomethyl]-3-cephem-4-carboxylic acid.

To a solution of 202 mg. (1.1 mmole) of 2-(1H-tetrazol-5-ylmethyl)-2H-tetrazol-5-thiol in 6 ml. of pH 7 buffer (solution was obtained with 176 mg. 2.1 mmole, of sodium bicarbonate) were added 460 mg. (1 mmole) of 7β-[α-methoximino-α-(2-amino-1,3-thiazol-4-yl)acetamido]cephalosporanic acid, and the solution was heated in an oil bath for 22 hours at a temperature of about 55° C. to about 60° C. After this time, a thin layer chromatogram of the reaction mixture indicated that the reaction was about one-half completed. An additional 100 mg. of the thiol and an equivalent amount of sodium bicarbonate were added to the reaction mixture. The reaction mixture was then heated for about 12 hours at a temperature of 55°-60° C. The reaction mixture was cooled to room temperature and was washed twice with 50 ml. portions of ethyl acetate. The aqueous phase was filtered, and the filtrate cooled in an ice bath to a temperature of about 0° C. The pH of the aqueous phase was adjusted to 3.2 with vigorous stirring, and the product precipitated as a yellow-orange precipitate. The product was filtered, washed with water, and dried at room temperature in vacuo. There were obtained 153 mg. of a mixture of the syn and anti forms of the product. The isomers were separated over reverse phase silica gel using 15% acetonitrile, 2% acetic acid, 83% water, v:v:v. syn Isomer NMR (360 MHz, DMSOd$_6$): δ3.65 (m, 2H, C-2 methylene), 3.85 (s, 3H, oxime methyl), 4.27 (m, 2H, C-3' methylene), 5.13 (d, 1H, C-6H), 5.82 (q, 1H, C-7H), 6.42 (s, 2H, methylene bridging tetrazole rings), 6.78 (s, 1H, thiazole H), 7.29 (broad s, 2H, thiazole amino), and 9.61 (d, 1H, 7-amide H) ppm. anti Isomer NMR (360 MHz, DMSOd$_6$): δ3.60 (m, 2H, C-2 methylene), 3.95 (s, 3H, oxime methyl), 4.27 (m, 2H, C-3' methylene), 4.97 (d, 1H, C-6H), 5.76 (q, 1H, (C-7H), 6.33 (s, 2H, methylene bridging tetrazole rings), 7.14 (broad s, 2H, thiazole amino H), 7.46 (s, 1H, thiazole H), and 9.43 (d, 1H, 7-amide H) ppm.

EXAMPLE 6

7-(2-Thienylacetamido)-3-[1-(1H-tetrazole-5-ylmethyl)-1H-tetrazole-5-ylthiomethyl]-3-cephem-4-carboxylic acid.

A solution of 808 mg. (2 mmole) of sodium 7-(2-thienylacetamido)-3-acetoxymethyl-3-cephem-4-carboxylate (sodium cephalothin), 368 mg. (2 mmole) of 1-(1H-tetrazole-5-ylmethyl)-1H-tetrazole-5-thiol, and 168 mg. (2 mmole) of sodium bicarbonate in 16 ml. of water was heated in an oil bath for 7 hours at a temperature between about 55° C. and about 60° C. The reaction mixture was concentrated under vacuum to a volume of about 8 ml. and injected onto reverse phase silica gel preparative HPLC. Separation was achieved by first using 15% acetonitrile:2% acetic acid by volume in water. Multiple 20 ml. fractions were collected and after about 90 fractions were collected, the eluent was changed to 20% acetonitrile in water. Fractions 133-153 containing the product were combined and evaporated. There were obtained 350 mg. of crystalline product as the p-nitrobenzyl ester. Fractions 181-193 contained the starting material sodium cephalothin.

The following data were obtained for the crystalline product.

NMR (100 MHz, DMSO-d$_6$): δ3.63 (m, 2H, C-2 methylene), 3.73 (s, 2H, thiopheneacetyl methylene), 4.32 (m, 2H, C-3' methylene), 5.04 (d, 1H, C-6H), 5.63 (q, 1H, C-7H), 5.97 (s, 2H, tetrazole methylene), 6.8-7.4 (m, 3H, thiophene H), and 9.08 (d, 1H, 7-amide H) ppm.

Elemental analysis:
Theory: C, 39.22; H, 3.10; N, 26.91
Found: C, 38.86; H, 3.33; N, 25.11.

IR (KBr) β-lactam carbonyl absorption at 1775 cm$^{-1}$.

Field Desorption Mass Spectrum: MW=521.

EXAMPLE 7

7-(2-thienylacetamido)-7-methoxy-3-[1-(1H-tetrazole-5-ylmethyl)-1H-tetrazole-5-ylthiomethyl]-3-cephem-4-carboxylic acid.

A solution of 3.1 g. (5.3 mmole) of p-nitrobenzyl 7-(2-thienylacetamido)-7-methoxy-3-bromomethyl-3-cephem-4-carboxylate and 1.38 g. (7.5 mmole) of 1-(1H-tetrazole-5-ylmethyl)-1H-tetrazole-5-thiol in 20 ml. of DMF was stirred at room temperature for about 16 hours. The reaction mixture was poured into 150 ml. of a mixture of equal volumes of 1 N hydrochloric acid and ethyl acetate. The organic layer was separated, washed twice with 1 N hydrochloric acid, once with brine, and was dried over sodium sulfate, filtered, and evaporated to dryness. There were obtained 3 g. of the impure product as a light brown foam. The product was chromatographed over 75 g. of silica gel using 1 liter of methylene chloride followed by two liters of methylene chloride containing 2% methyl alcohol for elution. The column was maintained under nitrogen pressure during elution. The fractions containing the product were combined and evaporated to dryness. The residual oil was dissolved in ethyl acetate and the solution was filtered. The filtrate was concentrated under vacuum to dryness. There was obtained 0.84 g. of the product.

The above product was deesterified by electrolytic reduction as follows: A solution of 700 mg. (1 mmole) of the p-nitrobenzyl ester in 30 ml. of 1 N sulfuric acid in DMF was placed in an electrolysis cell comprising a mercury pool cathode and a platinum wire anode. The electrodes were separated by a sintered glass frit. The reduction was carried out at a potential of −0.64 v over 3 hours. The reduction solution was removed from the cell and was poured into 100 ml. of a mixture of equal volumes of ethyl acetate and 1 N hydrochloric acid. The organic layer was separated and washed twice with 1 N hydrochloric acid. The product was then extracted from the organic layer with 50 ml. of aqueous sodium hydroxide, pH 7.5 and the aqueous extract was washed with ethyl acetate. The aqueous phase was layered with fresh ethyl acetate and acidified to pH 2.2 with hydrochloric acid. The organic layer was separated, washed twice with 1 N hydrochloric acid, with brine, dried over sodium sulfate and evaporated to dryness. There were obtained 290 mg. of the product in the free acid form as a yellow foam.

The product was purified as follows: The product, 270 mg. was dissolved in 0.05 M ammonium acetate by adding two drops of concentrated ammonium hydroxide to the suspension of the product and the solution was filtered and injected onto a reverse phase silica gel HPLC preparative column. The column was initially eluted with 12% acetonitrile:2% acetic acid:water and then with 15% acetonitrile:2% acetic acid:water. Multiple 20 ml. fractions were collected and fractions 72–89 were combined and lyophilized. There were obtained 75 mg. of the product as a dry powder.

The following data were obtained for the product.

IR (KBr) β-lactam carbonyl absorption at 1775 cm$^{-1}$.

Field Desorption Mass Spectrum: MW=551.

NMR (100 MHz, DMSO-d$_6$): δ3.34 (s, 3H, 7-methoxy), 3.51 (m, 2H, C-2 methylene), 3.80 (s, 2H, thiopheneacetyl methylene), 4.29 (m, 2H, C—3' methylene), 5.06 (s, 1H, C—6H), 5.97 (s, 2H, tetrazole methylene), 6.9–7.4 (m, 3H, thiophene ring H), and 9.42 (s, 1H, 7-amide H) ppm.

EXAMPLE 8

7-(O-Formylmandelamido)-3-[1-(1H-tetrazole-5-ylmethyl)-1H-tetrazole-5-thiol]-3-cephem-4-carboxylic acid.

To a solution of 1.01 g. (5.5 mmole) of 1-(1H-tetrazole-5-ylmethyl)-1H-tetrazole-5-thiol in 15 ml. of pH 7.0 buffer containing 0.88 g. of sodium bicarbonate were added 2.28 g. (5 mmole) of sodium 7-(O-formylmandelamido)-3-acetoxymethyl-3-cephem-4-carboxylate and the solution was heated with stirring at a temperature of about 60° C. to about 65° C. for 16 hours. The reaction mixture was cooled to room temperature and was concentrated to a volume of 6.5 ml. by evaporation in vacuo. The concentrate was chromatographed in silica gel reverse phase HPLC using 12% acetonitrile:2% acetic acid:water as eluent. Multiple 20 ml. fractions were collected and monitored by UV for the cephem chromophore content. Fractions 94–107 were combined and lyophilized. There were obtained 120 ml. of the title compound.

NMR (90 MHz, DMSO-d$_6$): signals at δ3.84 (m, C—2 methylene), 4.54 (m, C—3' methylene), 5.26 (d, C—6H), 5.32 (s, methine H of mandelamido side chain), 5.94 (q, C—7H), 6.24 (s, tetrazole methylene), 7.4–7.8 (m, phenyl H), and 9.04 (d, 7-amine H) ppm.

EXAMPLE 9

7-[α-(4-Ethylpiperazin-2,3-dione-1-ylcarbonylamino)-α-(4-hydroxyphenyl)acetamido]-3-[1-(1H-tetrazole-5-ylmethyl)-1H-tetrazole-5-ylthiomethyl]-3-cephem-4-carboxylic acid.

To a suspension of 8.3 g. (50 mmole) of 4-hydroxyphenylglycine in 75 ml. of tetrahydrofuran were added 25 ml. of bis-trimethylsilylacetamide and the suspension was stirred at room temperature for 15 minutes and then at 75° C. for 2.5 hours to form a solution. The solution was cooled to 0° C. and 25 ml. of propylene oxide were added. Next a solution of 11 g. of 4-ethylpiperazin-2,3-dione-1-ylcarbonyl chloride in 100 ml. of THF was added and the reaction mixture was stirred for 1 hour at 0° C. and at room temperature for 4 hours. Methyl alcohol, 40 ml., were added to the reaction mixture and after stirring for 15 minutes the mixture was evaporated to dryness. The gummy residue was dissolved in a mixture of ethyl acetate-aqueous sodium bicarbonate and the aqueous layer was separated, washed with ethyl acetate, filtered, and cooled to 0° C. The cold solution was layered with 200 ml. of fresh ethyl acetate and the pH adjusted to pH 1.9 with concentrated hydrochloric acid. The organic phase was separated, combined with an ethyl acetate wash of the acidified aqueous phase and dried over sodium sulfate. Evaporation of the dried organic phase gave 6.7 g. (40% yield) of α-(4-ethylpiperazin-2,3-dione-1-ylcarbonylamino)-4-hydroxyphenylacetic acid.

A solution of 670 mg. (2 mmole) of the acid and 306 mg. of hydroxybenzotriazole in 10 ml. of THF and containing 0.5 g. molecular sieve was stirred at room temperature for 1 hour, the solution cooled to 0° C. and 450 mg. of dicyclohexylcarbodiimide were added with continual stirring for 20 minutes. The reaction mixture was filtered to remove the sieve and dicyclohexylurea, and the filtrate was added to a 0° C. solution of 750 mg. (2 mmole) of 7-amino-3-[1-(1H-tetrazole-5-ylmethyl)-1H-tetrazole-5-ylthiomethyl]-3-cephem-4-carboxylic acid in 5 ml. of THF and 5 ml. of water containing 0.52 ml. of triethylamine. The reaction mixture was stirred at room temperature for about 16 hours and was evaporated in vacuo to remove the THF. The concentrate was diluted with 20 ml. of water and the pH adjusted to pH 7.0 with a 45% aqueous solution of potassium phosphate. The acidified solution was washed with 20 ml. of ethyl acetate, filtered, cooled to 0° C. and acidified to pH 1.9 with 20% hydrochloric acid. The product precipitated as a gum and the supernatant was decanted. Fresh water, 25 ml., were added to the gum and the mixture sonicated for 15 minutes until the product formed as a light brown solid. The product was filtered, washed with water and dried in vacuo at room temperature. There were obtained 750 mg. of the title compound.

The product was purified as follows. A suspension of 700 mg. of the above product in 6 ml. of 0.05 M ammonium acetate was treated with 2 drops of concentrated ammonium hydroxide to form a solution. The solution was injected onto a silica gel (C-18) reverse phase HPLC and chromatographed at 240 psi using 12:2:86; acetonitrile:acetic acid:water; v:v:v as eluent. Multiple fractions of about 20 ml. were collected. Fractions 104–120 were combined and evaporated to remove the acetonitrile. The aqueous residue was lyophilized to provide 87 mg. of the purified product containing a small amount of acetic acid.

NMR (90 MHz, DMSO-$d_6$): $\delta$1.25 (t, protons of methyl moiety of the 4-ethyl group), 3.4-4.2 (m, methylene protons of piperazine and C-2 methylene), 4.46 (m, C-3' methylene), 5.14 (d, C-6H), 5.62 (d, methine H of 4-hydroxyphenylacetyl group), 5.88 (q, C-7H), 6.08 (s, tetrazole methylene), 7.10 (m, 4-hydroxyphenyl H), 9.50 (d, $\alpha$-amide H), and 9.91 (d, C-7 amide H) ppm.

EXAMPLE 10 syn
7$\beta$-[$\alpha$-(Methoximino)-$\alpha$-(2-furyl)acetamido]-3-[1-(1H-tetrazol-5-ylmethyl)-1H-tetrazol-5-ylthiomethyl]-3-cephem-4-carboxylic acid.

A solution of sodium 7$\beta$-[$\alpha$-(methoximino)-$\alpha$-(2-furyl)acetamido]-3-acetoxymethyl-3-cephem-4-carboxylate, an equimolar amount of 1-(1H-tetrazol-5-ylmethyl)-1H-tetrazole-5-thiol and an equimolar amount of sodium bicarbonate in water is heated for about 24 hours at a temperature of about 55° C. The reaction mixture is concentrated under reduced pressure and the product is isolated from the concentrate by silica gel reverse phase HPLC.

The following preparations illustrate the preparation of the bis-tetrazole methyl thiols used to prepare the cephalosporin compounds of the invention.

Preparation of 1-cyanomethyl-1-H-tetrazol-5-ylthiol

A. Ethyl azidoacetate

To a solution of 490 g. (4 moles) of ethyl chloroacetate in 1500 ml. of acetonitrile were added 260 g. (4 moles) of sodium azide, and the mixture was heated at the reflux temperature for 20 hours. After heating, the reaction mixture was poured into 1 liter of water with stirring for ½ hour. The organic phase was separated from the aqueous phase and evaporated in vacuo to dryness. The yellow residual oil was dissolved in 1200 ml. of diethyl ether and the solution was dried over magnesium sulfate. Evaporation of the diethyl ether in vacuo gave 391 g. (76% yield) of ethyl azidoacetate.

B. Ethyl 5-chloro-1H-tetrazol-1-ylacetate

A mixture of 130 g. (1 mole) of ethyl azidoacetate prepared as described in part A and 96 g. (1.56 mole) of cyanogen chloride was heated at a temperature of 125° C. for 20 hours. After the reaction mixture had cooled, the reaction product mixture was dissolved in ethyl acetate, and the solution was filtered and evaporated in vacuo yielding a yellow crystalline mass of product. The yellow crystals were recrystallized from aqueous ethyl alcohol and gave 149 g. (78% yield) of ethyl 5-chloro-1H-tetrazol-1-ylacetate as pale yellow crystals melting at about 57°–60° C.

C. Ethyl 5-thiol-1H-tetrazol-1-ylacetate

A solution of 209 g. of the chlorotetrazole ester, prepared as described in part B above, and 250 g. of sodium hydrosulfide in 5 liters of ethyl alcohol was heated at the reflux temperature for 24 hours. After heating, the reaction mixture was acidified with concentrated hydrochloric acid, and the volume of the acidified mixture was reduced to ¼ the original volume by evaporation in vacuo. The concentrate was extracted with ethyl acetate, the extract was dried and evaporated to dryness under reduced pressure. The residual product was recrystallized from toluene-methylene chloride-hexane and gave 129 g. of the product.

D. 5-Thiol-1H-tetrazol-1-ylacetamide ammonium salt

A solution of 20 g. (0.106 mole) of the tetrazolthiol ester, prepared as described above in part C, in 320 ml. of concentrated ammonium hydroxide and 200 ml. of ethyl alcohol containing 500 ml. of ammonium chloride was heated at the reflux temperature for about 12 hours. After heating, the reaction mixture was evaporated in vacuo, and the yellow crystalline residue obtained was recrystallized from hot ethyl alcohol to yield a first crop of 13.7 g. (73% yield) of the product as white crystals melting at about 197 to about 199° C. after vacuum drying. A second crop of 1.4 g. of the product was obtained which melted at about 191°–193° C.

E. 1-Cyanomethyl-1H-tetrazol-5-thiol

A suspension of 5.28 g. of the tetrazolamide ammonium salt, prepared as described above in part D, in 90 ml. of methylene chloride containing 14.4 ml. of pyridine was cooled to a temperature of about 0° C. To this suspension was added dropwise with stirring a solution of 4.6 g. (30 mmole) of phosphorous oxychloride in 40 ml. of methylene chloride. After the addition was completed, the reaction mixture was heated at the reflux temperature for 30 minutes and was then cooled to room temperature with stirring. The reaction mixture had turned orange after heating and contained some precipitate. The reaction mixture was evaporated to dryness in vacuo and the residue dissolved in ethyl acetate-water, 1:1, v:v. The pH of the solution was adjusted to pH 2 with 20% aqueous hydrochloric acid. The acidified solution was then extracted twice with 75 ml. portions of ethyl acetate and the extracts combined. The extract was then washed with 5% hydrochloric acid, with brine, was dried over sodium sulfate and evaporated in vacuo. The brown oil was obtained as a residue and crystallized on standing. The crystals were vacuum dried at room temperature and yielded after drying 2.6 g. (61% yield) of light brown product melting at about 113°–114° C.

The above reaction was repeated on a 10.6 g. batch of the tetrazol amide ammonium salt and 3.7 g. of the nitrile as off-white crystals melting at about 116°–118° C. were obtained.

The following analytical data were obtained for the crystalline product.

Elemental analysis calculated for $C_3H_3N_5S$:
Theory: C, 25.53; H, 2.14; N, 49.62.
Found: C, 25.82; H, 2.40; N, 49.91.

The mass spectrum of the crystalline product showed a molecular weight of 141 in agreement with the product.

EXAMPLE 1

1-(1H-Tetrazol-5-ylmethyl)-1H-tetrazol-5-thiol

A solution of 6.0 g. (42.5 mmole) of 1-cyanomethyl-1H-tetrazol-5-thiol and 10.0 g. (6.3 mmole) of tetramethylguanidinium azide in 90 ml. of dioxane was heated at the reflux temperature for 3 hours. After cooling, the reaction mixture was evaporated to dryness in vacuo and the residue dissolved in ethyl acetate:water, 1:1. The ethyl acetate layer was separated, and the pH of the aqueous layer was adjusted to pH 1.8 with 20% hydrochloric acid. The acidified aqueous layer was then extracted 3 times with 75 ml. portions of ethyl acetate, and the extracts were combined. The extract was then washed with 5% hydrochloric acid, with brine, was dried over sodium sulfate, and then evaporated in vacuo to dryness. The red oil obtained as a residue crystallized on seeding. The crystals were washed with ethyl acetate and with diethyl ether and were dried. There were obtained 3.7 g. of the bis-tetrazolmethyl thiol melting at about 173° C. to about 175° C. The filtrate from the first crop was evaporated to an oil and after seeding the oil, 0.3 g. of a second crop crystalline product was obtained. A third crop of 0.3 g. was obtained in the same manner. Total yield of product was 4.3 g. (55% yield).

The NMR spectrum of the product run in DMSO-$d_6$ showed a singlet at 5.9 ppm delta for the protons of the methylene group bridging the tetrazole rings.

EXAMPLE 2

1-(1-Methyl-1H-tetrazol-5-ylmethyl)-1H-tetrazol-5-thiol

A. 5-Chloro-N-methyl-1H-tetrazol-1-acetamide

A solution of 19.5 g. (0.102 mole) of ethyl 5-chloro-1H-tetrazol-1-acetate in 30 ml. of ethyl alcohol was cooled in a dry ice-propyl alcohol bath, and methylamine gas was passed into the solution for 5 minutes. The reaction mixture solidified and was washed with ethyl alcohol and diethyl ether and was dried on the steam bath. There was obtained 13.2 g. (74% yield) of the N-methylamide product as white crystalline yields melting at about 146° to about 148° C.

The following analytical data were obtained for the crystalline product.

Elemental analysis calculated for $C_4H_6N_5OCl$:
Theory: C, 27.36; H, 3.44; N, 39.89; Cl, 20.19.
Found: C, 27.59; H, 3.35; N, 39.65; Cl, 20.49.
NMR (DMSO-$d_6$): δ 2.7 (d, J=5 Hz, 3H, amide methyl), 5.28 s, 2H, $CH_2$), 8.53 (s, broad, 1H, N—H) ppm.

Molecular weight via mass spectrum = 175.5

B. 1-α-Methyl-1H-tetrazol-5-ylmethyl)-5-chloro-1H-tetrazole

To a suspension of 1.75 g. (10 mmole) of 5-chloro-N-methyl-1H-tetrazol-1-acetamide, prepared as described under A above, in 50 ml. of methylene chloride containing 0.8 g. of pyridine maintained at a temperature of about 0° C. was added with stirring excess phosphene. After addition was completle, the reaction mixture was stirred for 10 minutes without further cooling. The clear solution obtained on reaction was evaporated to dryness at a temperature of about 30° C. under reduced pressure. The residue containing the reaction product was suspended in 50 ml. of dioxane, and 2.4 g. (15.2 mmole) of tetramethylguanidinium azide were added to the suspension. The mixture was heated for 2 hours at the reflux temperature and after stirring overnight at room temperature, the reaction mixture was concentrated to near dryness under reduced pressure. The concentrate was dissolved in 30 ml. of water forming a pale yellow solution from which the product crystallized as colorless needles. The product was filtered and 0.4 g. of the crystalline product melting at about 138° C. to about 140° C. was obtained. A second crop of 0.5 g. of the product melting at about 136° C. to about 139° C. was isolated from the filtrate.

The following analytical data were obtained for the crystalline product.

Elemental analysis calculated for $C_4H_5N_8Cl$:
Theory: C, 23.95; H, 2.51; N, 55.86; Cl, 17.45.
Found: C, 24.17; H, 2.75; N, 55.81; Cl, 17.85,
NMR (DMSO-$d_6$): δ 4.27 (s, 3H, N-$CH_3$), 6.33 (s, 2H, $CH_2$) ppm.

C. 1-(1-Methyl-1H-tetrazol-5-ylmethyl)-1H-tetrazol-5-thiol

To a suspension of 0.5 g. (2.5 mmole) of the 5-chloro-bis-tetrazol, prepared as described in B above, in 40 ml. of ethyl alcohol was added 0.6 g. of sodium hydrosulfide. The mixture was heated at the reflux temperature for 16 hours, was cooled to room temperature, and filtered. The filtrate was concentrated to near dryness under reduced pressure and 30 ml. of 5% hydrochloric acid were added. The acidified concentrate was extracted 3 times with 30 ml. portions of ethyl acetate, and the extracts were combined and washed with 5% hydrochloric acid, brine, and dried over sodium sulfate. The dried extract was concentrated to a small volume from which the crystalline product precipitated. The product was recrystallized from ethyl acetate-hexane, and there was obtained 0.3 g. of the product as nearly colorless crystals melting at about 190° C. to about 192° C.

The following analytical data were obtained with the crystalline product.

Elemental analysis calculated for $C_4H_6N_8S$:
Theoryj: C, 24.24; H, 3.05; N, 56.53.
Found: C, 24.21; H, 3.28; N, 56.43.
NMR (DMSO-$d_6$): δ 4.22 (s, 3H, $CH_3$), 5.95 (s, 2H, $CH_2$), 10.57 (broad s, 1H, SH).

The molecular weight as determined by mass spectrum was 198.

2-(1H-Tetrazole-5-ylmethyl)-2H-tetrazole-5-thiol

A. 5-Benzylthio-1H-tetrazole

A solution of 30 g. (0.33 mole) of thiosemicarbazide and 51 g. (0.40 mole) of benzyl chloride in 500 ml. of ethyl alcohol was heated at the reflux temperature for about 3.5 hours. After heating, the reaction mixture was evaporated to dryness under reduced pressure and the residue was dissolved in water. The solution was washed with ethyl acetate and was added to a solution of 25 g. (0.36 mole) of sodium nitrite in 50 ml. of water. The solution was stirred for 15 minutes and then ethyl acetate was added. The organic layer was separated and washed with water, brine, and was dried over sodium sulfate. The dried ethyl acetate solution was evaporated under reduced pressure, and the product obtained as a residue was washed with methylene chloride and recrystallized from ethyl acetate. There were obtained 21 g. of the product melting at about 134° C. to about 136° C.

The following analytical data were obtained with the product.

Elemental analysis calculated for $C_8H_8N_4S$:
Theory: C, 49.98; H, 4.19; N, 29.14.
Found: C, 49.81; H, 4.17; N, 28.95.

B. 1- and 2-Cyanomethyl-5-benzylthio-1H-tetrazol

A solution of 2.7 g. of potassium hydroxide in 5 ml. of methyl alcohol was added with stirring to a solution of 7.9 g. (0.041 M) of 5-benzylthio-1H-tetrazole in 25 ml. of methyl alcohol, and after stirring the solution for 15 minutes at room temperature, 3.4 g. (0.045 M) of chloroacetonitrile was added. The reaction mixture was heated at the reflux temperature for about 12 hours and the white solid which formed was filtered. The filtrate was concentrated in vacuo to an oily residue, and the residue dissolved in a mixture of diethyl ether and water. The ether layer was separated and washed in an aqueous solution of sodium bicarbonate, water, and with brine, and was dried and evaporated to dryness under reduced pressure. There were obtained 3.4 g. of a mixture of 1- and 2-cyanomethyl-5-benzylthio-1H-tetrazol as a reddish oil. The nuclear NMR spectrum of the oil showed it was a mixture of approximately 50% of each of the isomers.

C. 5-Benzylthiol-2-(1H-tetrazol-5-ylmethyl) 2H-tetrazole

To 70 ml. of dry tetrahydrofuran cooled in an ice-ethanol bath were added in small portions 4.04 g. (0.03 mole) of anhydrous aluminum chloride. After addition was complete 5.85 g. (0.09 mole) of finely ground sodium azide were added with stirring. After stirring the mixture for 5 minutes a solution of 3.93 g. (0.017 mole) of the 1- and 2-cyanomethyl-5-benzylthiotetrazole isomeric mixture in 20 ml. of dry tetrahydrofuran was added and the mixture heated at the reflux temperature for 24 hours. The reaction mixture was cooled in an ice-ethanol mixture and acidified by dropwise addition of 30 ml. of 20% hydrochloric acid. The acidified mixture was concentrated under reduced pressure to a volume of about 30 ml. and the concentrate was extracted with three 30 ml. portions of ethyl acetate. The extracts were combined, washed with brine, and dried over anhydrous sodium sulfate. The dried extract was evaporated under vacuum to dryness providing 4.5 g. (97% yield) of a mixture of the isomeric 5-benzylthio-1-and 2-(1H-tetrazole-5-ylmethyl)-1H- and 2H-tetrazoles as a tan oil. After standing for several days, crystals formed in the oil. The mixture was triturated with methylene chloride and filtered to provide 0.85 g. of cream-colored crystals melting at about 115° C. to about 117° C. A second crop of crystals which weighed 0.2 g. was obtained from the filtrate.

The above preparation was repeated by reacting 7.1 g. of the isomeric 5-benzylthio-1- and 2-cyanomethyl-tetrazole with aluminum azide (formed as described above with 7.3 g. of aluminum chloride and 10.7 g. of sodium azide). After heating at the reflux temperature for 24 hours, the reaction mixture was acidified with 20% hydrochloric acid, evaporated to a volume of about 60 ml., extracted with ethyl acetate, the extract washed with brine, dried, and evaporated to dryness. The residue crystallized on standing. The cream-colored crystals were suspended in methylene chloride and filtered to provide 3.5 g. of crystalline material. The filtrate was evaporated to dryness to provide 4.9 g. of an orange oil.

The nmr spectrum of the crystalline product run in deuterated DMSO showed mainly one isomer, the 2-isomer, while the nmr spectrum of the oil showed mainly the 1-isomer.

D. 2-(1H-Tetrazole-5-ylmethyl)-2H-tetrazole-5-thiol

5-Benzylthio-2-(1H-tetrazole-5-ylmethyl)-2H-tetrazole, 175 mg., prepared as described above under part C, was dissolved in 40 ml. of distilled DMF and reduced at the mercury pool cathode (14 cm² Hg pool) with a platinium wire anode. The electrodes were separated by a glass frit. The electrolyte was tetraethylammonium perchlorate, 0.1 M in the DMF solution of the substrate. The electrolysis was carried out at −2.7 to −2.85 volts for 500 seconds at −2.80 v. for about 630 seconds.

The reduction product mixture from the one-electron reduction was evaporated to dryness and the residue of product dissolved in ethyl acetate. The solution was washed three times with a 9:1 by volume mixture of a saturated solution of sodium chloride and 0.1 N hydrochloric acid and was dried over anhydrous magnesium sulfate. The dried solution was concentrated in vacuo and 111 mg. of the title compound precipitated from the concentrate. The product was filtered and dried.

I claim:
1. A compound of the formula

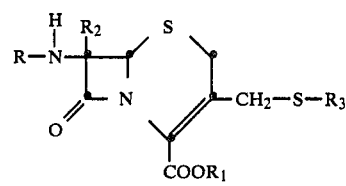

wherein R is an acyl group of the formula

wherein $R^1$ is $C_1$–$C_4$ alkyl or $C_1$–$C_4$ alkyl substituted by halogen or cyano; or R is an aroyl or aralkanoyl group of the formula

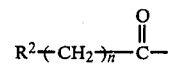

wherein $R^2$ is phenyl or a mono-substituted phenyl group substituted by halogen, cyano, amino, hydroxy, $C_1$–$C_4$ alkyl, $C_1$–$C_4$ alkoxy, carboxy, carboxamido, hydroxymethyl, aminomethyl, carboxymethyl, or $C_1$–$C_4$ alkoxycarbonylmethyl;

or $R^2$ is a di- or tri-substituted phenyl group of the formula

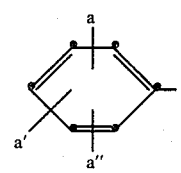

wherein a, a′, and a″ independently are hydrogen, halogen, hydroxy, $C_1$-$C_4$ alkoxy, provided that only one of a, a′ and a″ may be hydrogen, and n is 0 or 1;

or R is a heteroarylalkanoyl group of the formula $$R^3-CH_2-\overset{O}{\underset{\|}{C}}-$$

wherein $R^3$ is a group of the formula

[structures shown]

wherein each b is hydrogen, amino, protected-amino, $C_1$-$C_3$ alkyl or phenyl;

or R is an aryloxyacetyl or arylthioacetyl group of the formula $$R^2(Z)_n CH_2-\overset{O}{\underset{\|}{C}}-$$

wherein $R^2$ has the same meanings as defined above and Z is O or S;

or R is a substituted aralkanoyl or heteroarylalkanoyl group of the formula $$R^4-\underset{Q}{\overset{\text{}}{C}H}-\overset{O}{\underset{\|}{C}}-$$

wherein $R^4$ is $R^2$ as defined above, and in addition is 1,4-cyclohexadienyl, thienyl or furyl, and Q is hydroxy, formyloxy, carboxy, sulfo, or amino; or R is an oximino-substituted aralkanoyl or heteroarylalkanoyl group of the formula $$R^5-\underset{\underset{OR^6}{\overset{\|}{N}}}{C}-\overset{O}{\underset{\|}{C}}-$$

wherein $R^5$ is $R^2$ and $R^3$ as each is defined above, and $R^6$ is hydrogen, or $C_1$-$C_4$ alkyl, or R is a group of the formula $$R^4-\underset{\underset{\underset{R^7}{C=O}}{NH}}{\overset{\text{}}{C}H}-\overset{O}{\underset{\|}{C}}-$$

wherein $R^4$ has the same meanings defined above and $R^7$ is phenyl substituted by from 1 to 3 hydroxy groups, or pyridyl substituted by from 1 to 3 hydroxy groups, or a group of the formula $$R^8-\overset{O}{\underset{\|}{C}}-\underset{\underset{CH_3}{\text{}}}{N}-$$

wherein $R^8$ is $C_1$-$C_4$ alkylamino, phenyl, halophenyl, furyl, styryl, nitrostyryl or halostyryl; or $R^7$ is a group of the formula $$R^9-N\underset{(CH_2)_m}{\overset{(\overset{O}{\underset{\|}{C}})_{n'}}{\diagdown\diagup}}N-$$

wherein n′ is 1 or 2 and m is 2 or 3, with the limitation that when n′ is 2, m is 2, and $R^9$ is hydrogen, $C_1$-$C_3$ alkyl, $C_2$-$C_4$ alkanoyl, or $C_1$-$C_3$ alkylsulfonyl;

$R_1$ is hydrogen or a carboxy protecting group;
$R_2$ is hydrogen or methoxy;
$R_3$ is a bis-tetrazolylmethyl group of the formula

[structures shown]

wherein $R_4$ is hydrogen, or $C_1$-$C_3$ alkyl; and when $R_1$ is hydrogen the pharmaceutically acceptable, non-toxic salts thereof.

2. The compound of claim 1 wherein $R_3$ is a bis-tetrazolemethyl group of the formula

[structure shown]

3. The compound of claim 2 wherein R is an acyl group of the formula

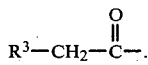

4. The compound of claim 3 wherein $R^3$ is thienyl or furyl.

5. The compound of claim 4 of the formula

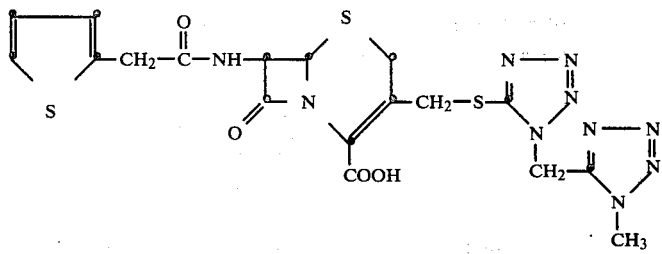

6. The compound of claim 4 of the formula

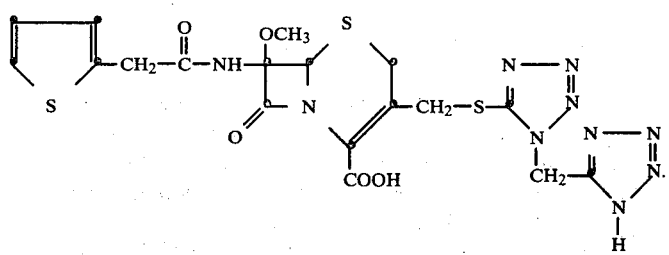

7. The compound of claim 2 wherein R is an acyl group of the formula

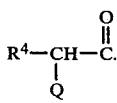

8. The compound of claim 7 wherein Q is hydroxy or formyloxy.

9. The compound of claim 8 of the formula

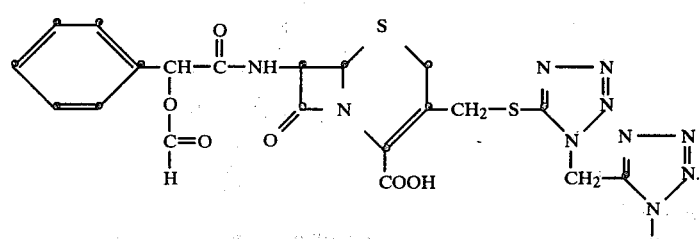

10. The compound of claim 2 wherein R is an acyl group of the formula

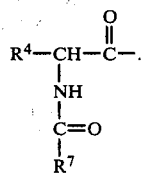

11. The compound of claim 10 wherein $R^7$ is a group of the formula

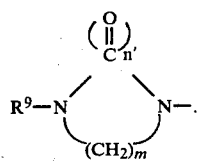

12. The compound of claim 11 of the formula

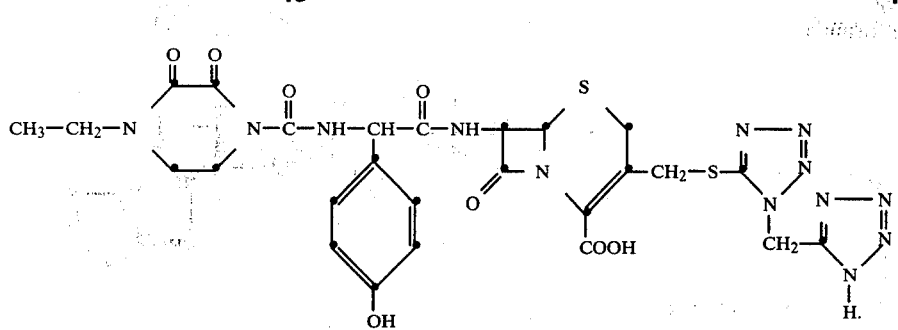

13. The compound of claim 2 wherein R is an acyl group of the formula

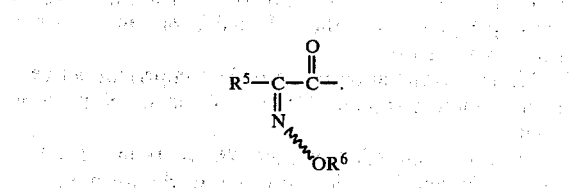

14. The compound of claim 13 wherein $R^5$ is a furyl or a 2-amino-1,3-thiazol-4-yl group.

15. The compound of claim 14 in the syn form.

16. The compound of claim 15 of the formula

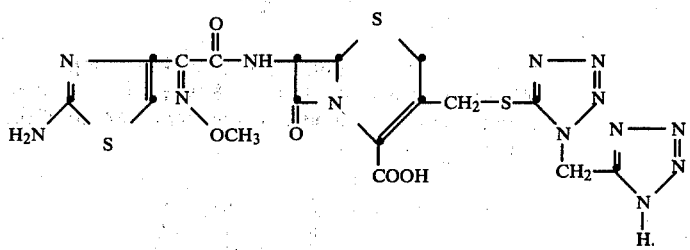

17. The compound of claim 15 of the formula

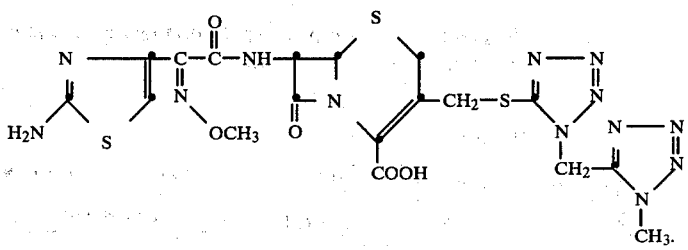

18. The compound of claim 1 wherein $R_3$ is a bis-tetrazolemethyl group of the formula

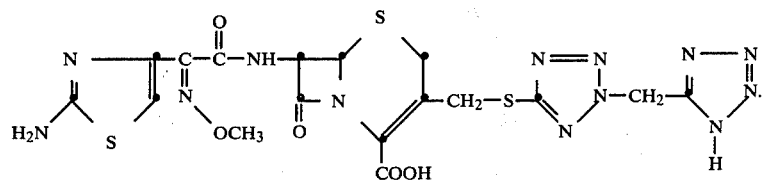

19. The compound of claim 18 wherein R is an acyl group of the formula wherein $R^5$ is a furyl or a 2-amino-1,3-thiazol-4-yl group.

20. The compound of claim 19 in the syn form.

21. The compound of claim 20 of the formula

22. The compound of the formula

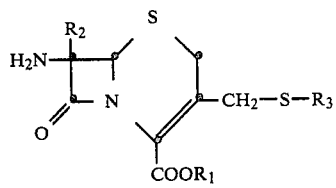

wherein $R_1$ is hydrogen or a carboxy-protecting group; $R_2$ is hydrogen or methoxy; and $R_3$ is a bis-tetrazolyl-methyl group of the formula

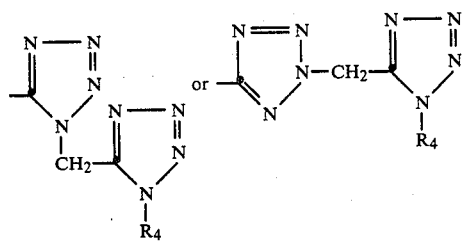

wherein $R_4$ is hydrogen or $C_1$–$C_3$ alkyl.

23. The compound of claim 22 wherein $R_3$ is a bis-tetrazolemethyl group of the formula

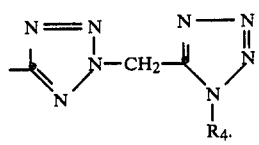

24. The compound of claim 22 wherein $R_3$ is a bis-tetrazolemethyl group of the formula

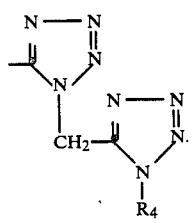

25. The compound of claim 24 of the formula

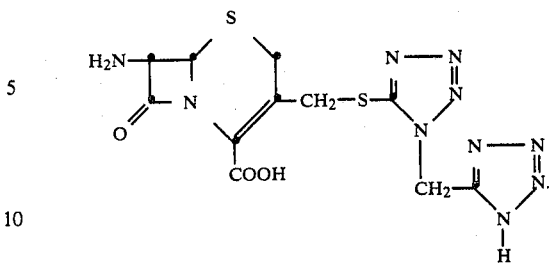

26. An antibiotic pharmaceutical formulation comprising an effective amount of an antibiotic compound of claim 1, wherein $R_1$ is hydrogen or a pharmaceutically acceptable salt thereof, and a pharmaceutically acceptable carrier.

27. The formulation of claim 26 comprising between about 50 mg. and about 500 mg. of the antibiotic compound.

28. The formulation of claim 26 where in the antibiotic compound R is an acyl group of the formula

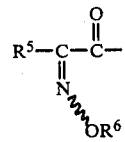

wherein $R^5$ is the 2-amino-1,3-thiazol-4-yl group.

29. The formulation of claim 28 where in the antibiotic compound $R_3$ is a bis-tetrazolemethyl group of the formula

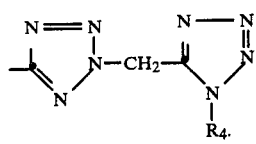

30. The formulation of claim 29 comprising the antibiotic compound of the formula

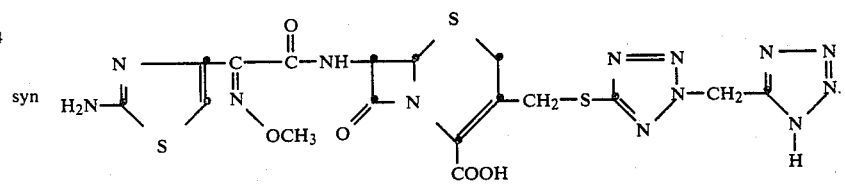

31. The formulation of claim 28 where in the antibiotic compound $R_3$ is a bis-tetrazolemethyl group of the formula

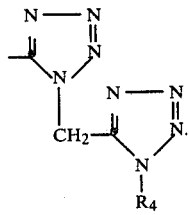

32. The formulation of claim 31 where in the antibiotic compound is selected from the group consisting of a compound of the formula
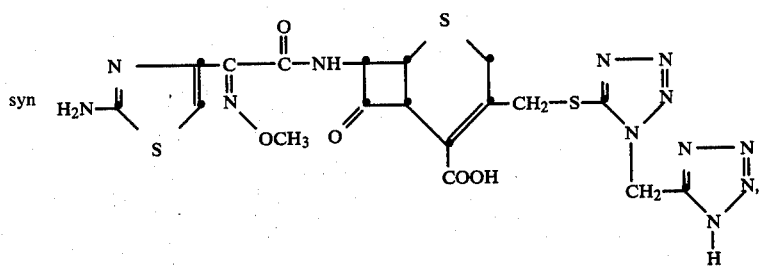
and a compound of the formula
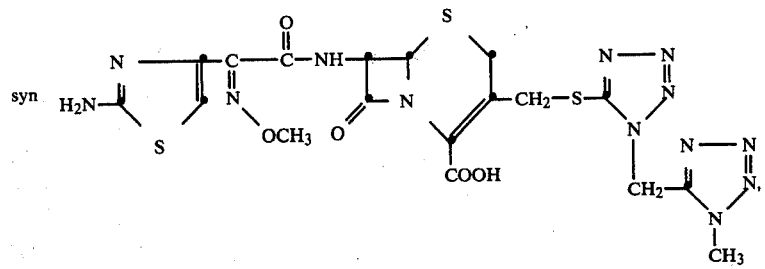
and a pharmaceutically acceptable salt thereof.
* * * * *